(12) United States Patent
Choi et al.

(10) Patent No.: US 10,585,849 B2
(45) Date of Patent: Mar. 10, 2020

(54) MEDICAL INFORMATION PROVIDING APPARATUS AND MEDICAL INFORMATION PROVIDING METHOD

(71) Applicant: Pusan National University Industry-University Cooperation Foundation, Geumjeong-gu, Busan (KR)

(72) Inventors: Byung Kwan Choi, Sasang-gu Busan (KR); Sang Wan Kim, Yeonje-gu Busan (KR); Seong Hyun Seo, Yangsan-si Gyeongsangnam-do (KR); Kye Young Park, Dong-gu Busan (KR); Won Seok Seong, Geumjeong-gu Busan (KR); Kyung Ho Lim, Geumjeong-gu Busan (KR); Ho Young Jeong, Busanjin-gu Busan (KR); Sung Moon Son, Dongnae-gu Busan (KR); Byeong Yong Kim, Yangsan-si Gyeongsangnam-do (KR); Ji Eun Kim, Sasang-gu Busan (KR); Ji Wuk Yoo, Haeundae-gu Busan (KR)

(73) Assignee: PUSAN NATIONAL UNIVERSITY INDUSTRY-UNIVERSITY COOPERATION FOUNDATION, Geumjeong-gu, Busan (KR)

( * ) Notice: Subject to any disclaimer, the term of this patent is extended or adjusted under 35 U.S.C. 154(b) by 272 days.

(21) Appl. No.: 15/548,291

(22) PCT Filed: Jan. 29, 2016

(86) PCT No.: PCT/KR2016/001013
§ 371 (c)(1),
(2) Date: Aug. 2, 2017

(87) PCT Pub. No.: WO2016/126056
PCT Pub. Date: Aug. 11, 2016

(65) Prior Publication Data
US 2018/0024995 A1    Jan. 25, 2018

(30) Foreign Application Priority Data
Feb. 3, 2015    (KR) ........................ 10-2015-0016667

(51) Int. Cl.
*G06F 17/30*    (2006.01)
*G06F 16/00*    (2019.01)
(Continued)

(52) U.S. Cl.
CPC .............. *G06F 16/00* (2019.01); *G06F 19/32* (2013.01); *G06K 9/62* (2013.01)

(58) Field of Classification Search
CPC ......... G06F 16/00; G06F 19/32; G06H 30/20; G06K 9/62; G06K 9/6211
(Continued)

(56) References Cited

U.S. PATENT DOCUMENTS

2011/0007954 A1* 1/2011 Suehling ............ G06K 9/00362
382/128

FOREIGN PATENT DOCUMENTS

JP    2001061839 A    3/2001
JP    2011010828 A    1/2011
(Continued)

OTHER PUBLICATIONS

Int'l Search Report dated May 4, 2016 in Int'l Application No. PCT/KR2016/001013.
(Continued)

*Primary Examiner* — Isaac M Woo
(74) *Attorney, Agent, or Firm* — Panitch Schwarz Belisario & Nadel LLP

(57) ABSTRACT

The present invention relates to a medical information providing apparatus that displays medical information on an
(Continued)

area extracted from a medical image and a medical information providing method therefor. The medical information providing apparatus according to the present invention may comprise: an acquisition unit for obtaining a medical image from a hospital server; an extraction unit for extracting a lesion image from the medical image; an image-matching unit for matching the lesion image onto a body map; and a processing unit for displaying medical information corresponding to the matched area on the body map to which the lesion image is matched with.

12 Claims, 32 Drawing Sheets

(51) Int. Cl.
G06K 9/62 (2006.01)
G06F 19/00 (2018.01)
(58) Field of Classification Search
USPC .................................. 707/600–899
See application file for complete search history.

(56) References Cited

FOREIGN PATENT DOCUMENTS

| KR | 20100065194 A | 6/2010 |
| KR | 20120110480 A | 10/2012 |
| KR | 20130023735 A | 3/2013 |
| KR | 101287382 B1 | 7/2013 |
| KR | 20140049137 A | 4/2014 |
| KR | 20140104946 A | 8/2014 |
| KR | 20150006807 A | 1/2015 |

OTHER PUBLICATIONS

Written Opinion dated May 4, 2016 in Int'l Application No. PCT/KR2016/001013.
Cho et al, "A Development of Reference Terminology Subset Editor for Effective Adaption of Clinical Vocabulary," Jounral of Korea Multimedia Society, vol. 11, No. 3, pp. 364-372 (2008).

* cited by examiner

FIG. 2
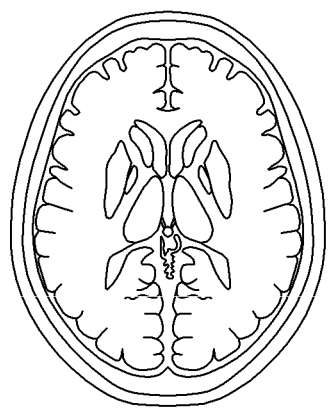
210
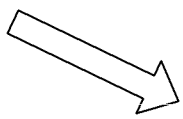
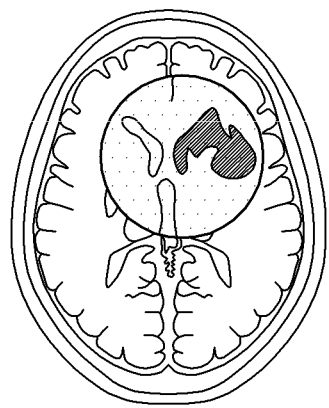
230
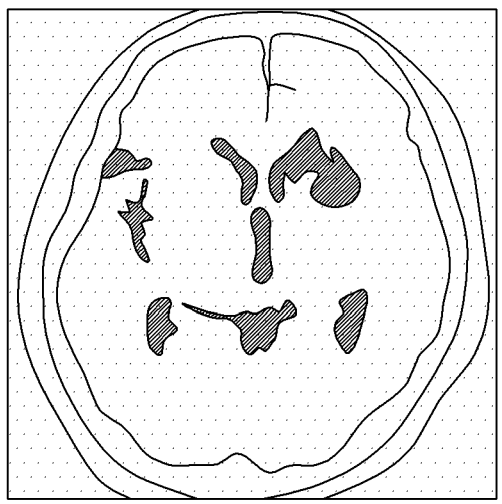
220

FIG. 10
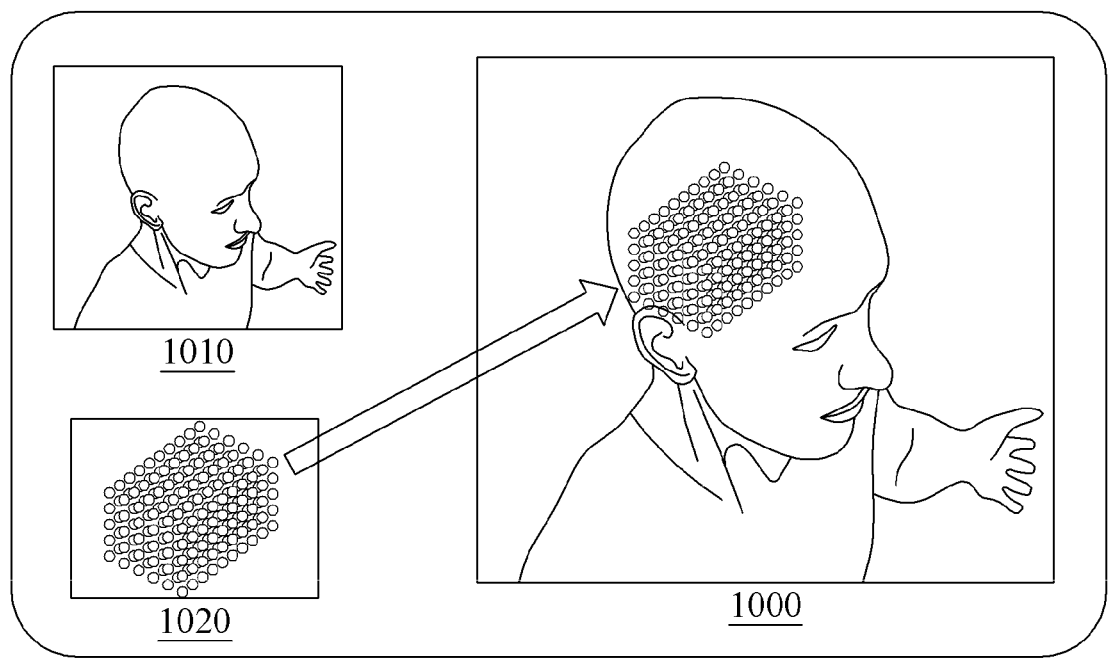
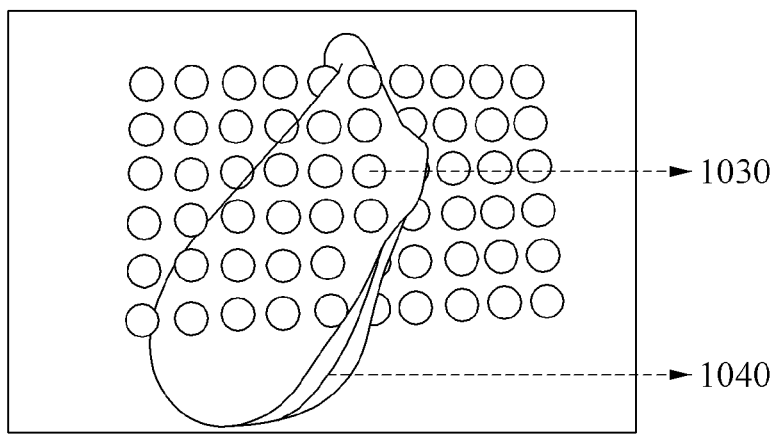

- Lesion is (bright).
- Edge is (uneven).
- Volume is (00).
- Bright and dark parts are mixed.

1510

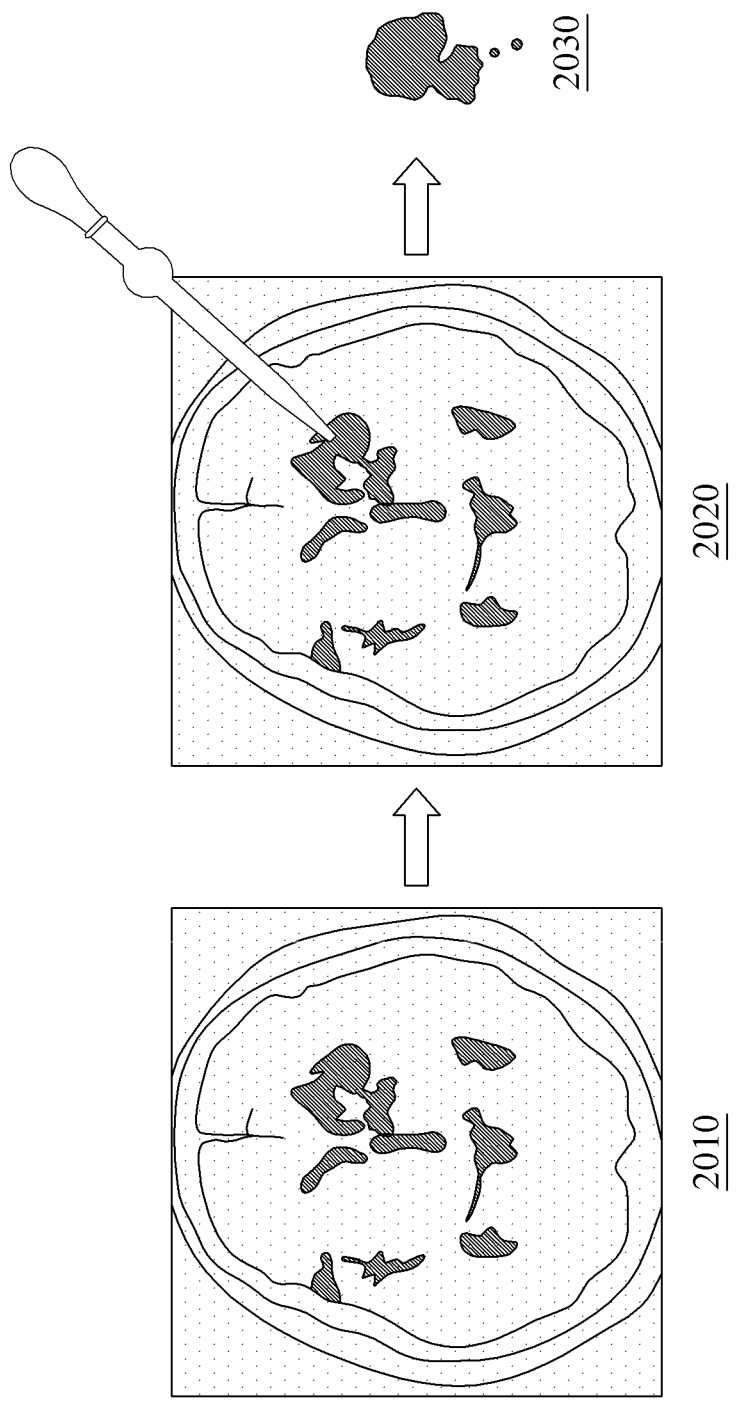

FIG. 21

Note of ultrasonography (abdomen)

No evidence of abnormal echogenic lesion in liver and pancreas.
Non delineation of stone echogenesities in GB and biliary trees
  without ductal dilatation.
Normal shape and size of liver with mild increased liver
  parenchymal echogenesities compared with right
  renal cortical echogenesities.
No evidence of abnormal echogenic lesion in both kidneys.

FIG. 22

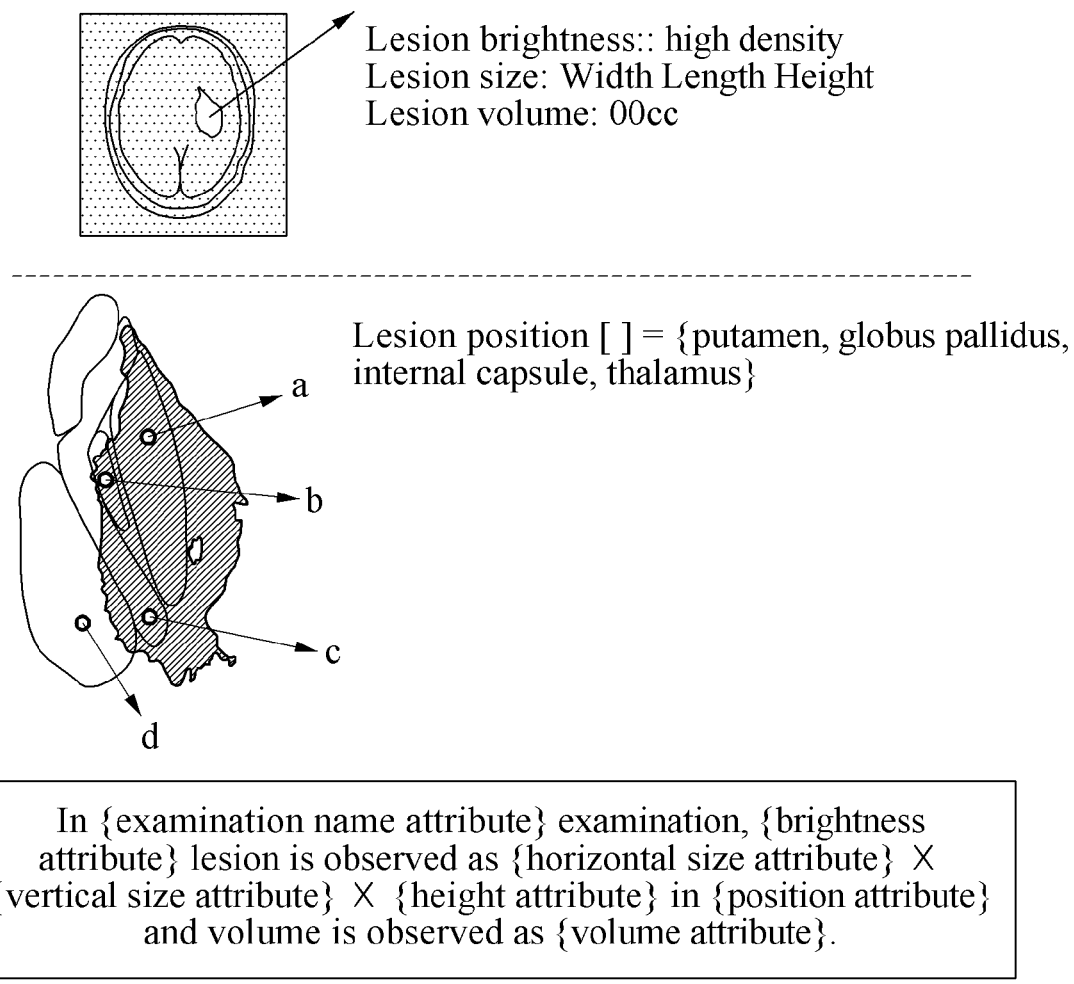

Lesion brightness:: high density
Lesion size: Width Length Height
Lesion volume: 00cc Lesion position [ ] = {putamen, globus pallidus, internal capsule, thalamus}

In {examination name attribute} examination, {brightness attribute} lesion is observed as {horizontal size attribute} X {vertical size attribute} X {height attribute} in {position attribute} and volume is observed as {volume attribute}.

⇩

In {brain CT} examination, {high density} lesion is observed as {horizontal size attribute} X {vertical size attribute} X {height attribute} in {putamen, globus pallidus, internal capsule, thalamus} and volume is observed as {00 cc}.

MEDICAL INFORMATION PROVIDING APPARATUS AND MEDICAL INFORMATION PROVIDING METHOD

CROSS-REFERENCE TO RELATED APPLICATIONS

This application is a Section 371 of International Application No. PCT/KR2016/001013, filed Jan. 29, 2016, which was published in the Korean language on Aug. 11, 2016, under International Publication No. WO 2016/126056 A1, the disclosure of which is incorporated herein by reference.

TECHNICAL FIELD

The present invention relates to a medical information providing method and a medical information providing apparatus for displaying medical information of an area extracted from a medical image.

BACKGROUND ART

Various medical imaging devices have been used to track a lesion of a patient. For example, a computed tomography (CT) device may be used to acquire a lesion and a component based on a horizontal cross section of a body. Also, a magnetic resonance imaging (MRI) device may be used to acquire a lesion and a component from a medical image of a desired cross section obtained through, for example, transverse imaging, coronal imaging, and sagittal imaging.

In recent years, it is possible to extract specific lesion area from a medical image by computer vision technology. The technique may include, for example, a technique for extracting only a blood vessel or a tumor and a technique for displaying a composite image of only a skull bone.

A general medical image may simply display a specific body area and thus, a diagnosis of a lesion area or reading medical image must be performed by a medical staff. Such reading process may derive subjective results depending on individual medical staff and the radiology report may be inconsistent. Also, when recording the medical information, medical terminology codes have to be assigned manually. However, the number of codes in standard terminology system is enormous and such terminology system tends to be updated over time. Thus, lots of time and efforts may be required for finding and updating diagnosis name codes in the medical information system.

Also, with the development of medical imaging devices and computing technology, a use of three-dimensional (3D) medical image is also increasing. However, a development of a technique for assigning a diagnosis and medical terminology code corresponding to a 3D medical image may be insufficient.

Accordingly, there is a desire for a method and apparatus for automatically displaying a diagnosis name and assigning medical terminology code of a lesion extracted from a medical image corresponding to a 2D image or a 3D image.

DISCLOSURE OF INVENTION

Technical Goals

An aspect of the present invention is to display a lesion image registered to a body map to which an attribute node is mapped and medical information obtained from the lesion image and to store the lesion image and the medical information, thereby accurately and easily acquiring medical information including a diagnosis name and a diagnosis name code of the lesion image.

Another aspect of the present invention is to store medical information matching a lesion image, thereby providing a database for displaying accurate medical information based on the medical information matching the stored lesion image.

Technical Solutions

According to an aspect, there is an apparatus for providing medical information, the apparatus including an acquirer configured to acquire a medical image from a hospital server, an extractor configured to extract a lesion image from the medical image, a registration module configured to register the lesion image to a human body model (body map), and a processor configured to display medical information corresponding to an area in the body map registering the lesion image.

According to another aspect, there is also provided a method of providing medical information, the method including acquiring a medical image from a hospital server, extracting a lesion image from the medical image, registering the lesion image to a body map, and displaying medical information corresponding to an area in the body map associated with the lesion image.

Effects

According to an aspect of the present invention, it is possible to display medical information on a two-dimensional (2D) or three-dimensional (3D) lesion image to which attribute nodes are mapped, thereby reducing time for producing medical information including diagnosis and medical terminology code from the lesion image.

According to another aspect of the present invention, it is possible to store a lesion image and medical information associated with the lesion image, thereby providing a database for displaying objective and accurate medical information.

BRIEF DESCRIPTION OF DRAWINGS

FIG. 2 is a diagram illustrating a matching process according to an example embodiment.

FIGS. 9 and 10 are diagrams illustrating examples of a human body map to which an attribute node is mapped.

FIGS. 19 and 20 are diagrams illustrating examples of extracting a lesion image from a medical image according to an example embodiment.

FIGS. 21 and 22 are diagrams illustrating examples of outputting a formatted document according to an example embodiment.

BEST MODE FOR CARRYING OUT THE INVENTION

Figure 1:
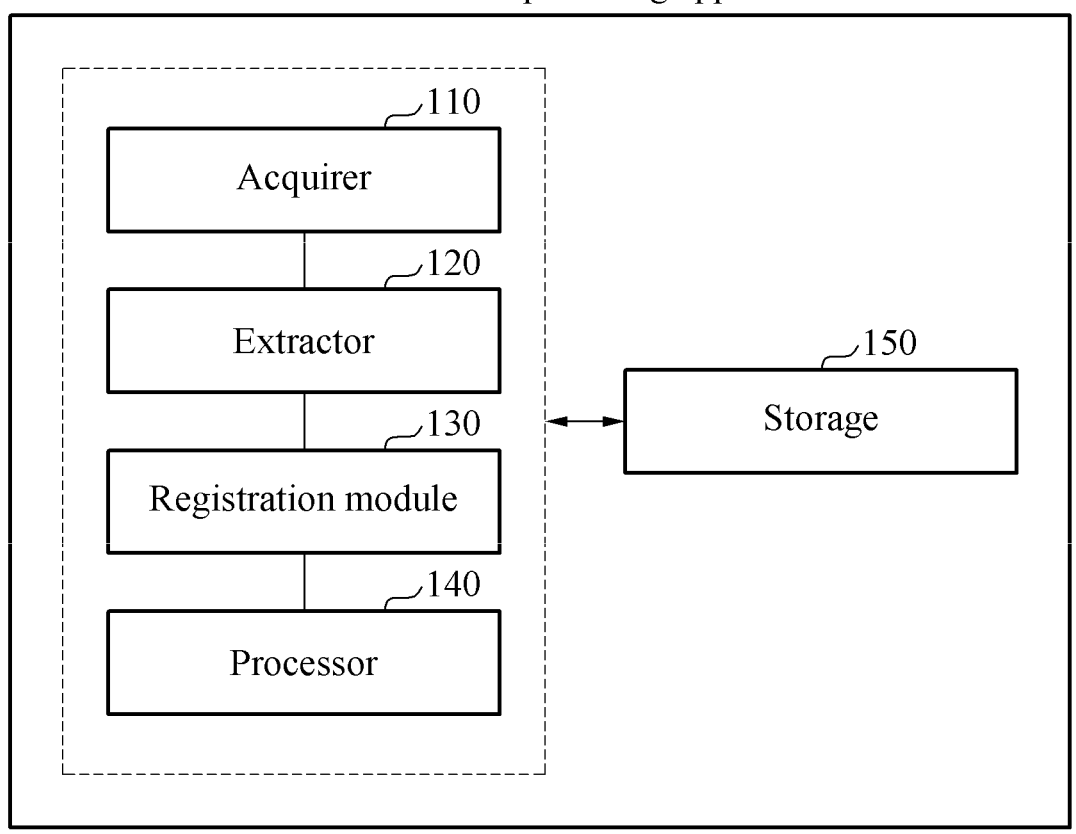
FIG. 1 is a block diagram illustrating a medical information providing apparatus according to an example embodiment.

Reference will now be made in detail to embodiments of the present invention, examples of which are illustrated in the accompanying drawings, wherein like reference numerals refer to the like elements throughout. The embodiments are described below in order to explain the present invention by referring to the figures.

In the present disclosure, medical information may include at least one medical terminology system. The medical terminology system may be, for example, Systematized Nomenclature of Medicine (SNOMED), International Classification of Diseases (ICD), Current Procedural Terminology (CPT) system, Unified Medical Language System (UMLS), International Classification for Nursing Practice (ICNP), and Logical Observation Identifiers Names and Codes (LOINC). Hereinafter, the medical information including 'SNOMED code' will be described but not limited thereto.

A medical information providing apparatus and a medical information providing method may display medical information using a body map registered with an extracted lesion image, thereby easily providing medical information for a lesion among a large amount of medical information.

FIG. 1 is a block diagram illustrating a medical information providing apparatus according to an example embodiment.

A medical information providing apparatus 100 may include an acquirer 110, an extractor 120, a registration module 130, and a processor 140. Also, depending on examples, the medical information providing apparatus 100 may additionally include a storage 150.

The acquirer 110 may acquire a medical image from a hospital server. Here, the medical image may be an image acquired by at least one medical imaging device, data stored in the hospital server, or a picture represented two-dimensionally or three dimensionally. The image acquired by the medical imaging device may be an image captured through, for example, X-ray imaging, computed tomography (CT), magnetic resonance imaging (MRI), single photon emission computed tomography (SPECT), and positron emission tomography (PET) but not limited thereto.

The extractor 120 may extract a lesion image from the medical image. For example, the extractor 120 may extract an image suspected to be a lesion from the medical image.

In this example, the extractor 120 may extract the lesion image as at least one of a two-dimensional (2D) image and a three-dimensional (3D) image. That is, the medical image may be a 2D image or a 3D image. The extractor 120 may extract the lesion image as a 2D image or a 3D image.

Also, the extractor 120 may extract the lesion image only for a specific tissue among various human body tissues. When extracting only a lesion image of a bone from a medical image of a head, the extractor 120 may extract only the lesion image of the skull bone.

An example of extracting the lesion image will be also described with reference to FIGS. 17A, 17B, 19, and 20 and thus, repeated description will be omitted for brevity.

The registration module 130 may register the lesion image to a body map. In this example, the registration module 130 may register the lesion image and a body map by anatomical relationship. Before describing the body map, the registration module 130 will be described with reference to FIG. 2.

FIG. 2 is a diagram illustrating a registration process according to an example embodiment.

Referring to FIG. 2, the registration module 130 may register a medical image 220 or a lesion image such that an anatomical region corresponds to an anatomical region of a body map 210. As shown by a registered area 230 of FIG. 2 (in circle), the registration module 130 may register anatomically coincident areas. Also, the registration module 130 may register the body map 210 and the medical image 220 or the lesion image based on a reference corresponding to a combination of at least one of a point, a line, an area, and a space.

The registration module 130 may represent the registered area 230 using coordinates. A lesion image extracted before the body map 210 is registered may be represented as coordinates on the medical image 220. When the registered area 230 is generated after the registration, the coordinates of the lesion image on the medical image 220 may be represented by a coordinate system on the body map 210. Thus, the registration module 130 may represent the registered lesion image as coordinates on the body map 210.

Hereinafter, a body map will be described.

The body map may be a 2D image or a 3D image illustrating an anatomical area of a human body and may include medical information corresponding to various areas. In terms of an area in which a predetermined point, line, plane, or space is distributed, the body map may indicate an anatomical concept for a given region in it. In this example, the predetermined point, line, plane, or space may express a lesion image of an area affected by a disease in a body.

The body map may include medical information on a disease that may occur in the corresponding anatomical area. Here, the medical information may include information including a diagnosis name, a terminology system code, a medicine or treatment method corresponding to the region. The medical information will also be described in detail with reference to FIG. 12.

The body map may be a medical image that has been already registered to another body map. For example, the body map may be a medical image with a coordinate system that has been divided into small anatomical areas. Also, the body map may be a medical image in which another image is applied as a texture. This may be used as a reference image when the registration module 130 register another medical image or may allow a user to easily understand the body map. Examples of the body map will be described with reference to FIGS. 3, 4A, and 4B.

Figure 3:
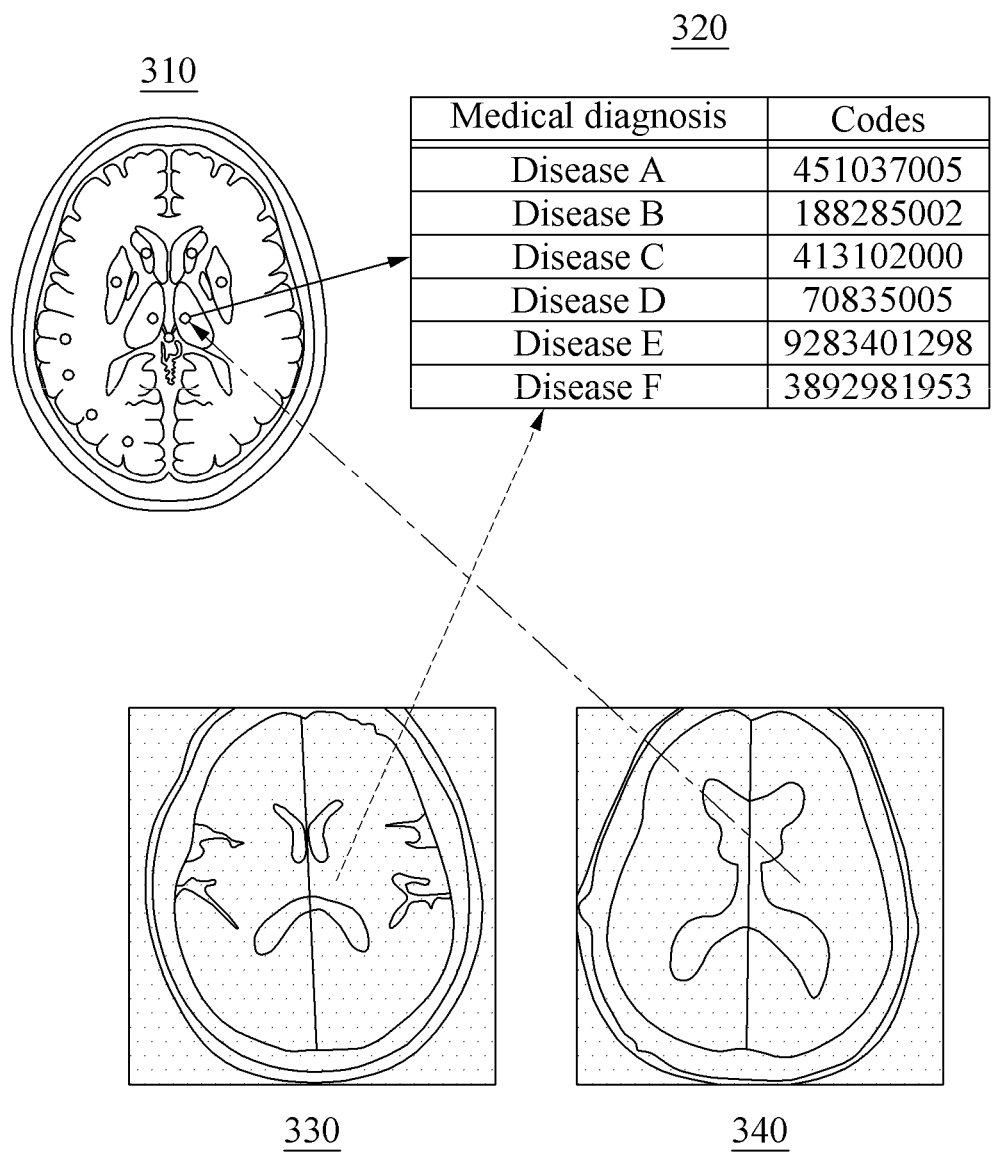
FIGS. 3, 4A, and 4B illustrate examples of a body map.
Figure 4A:
Figure 4B:
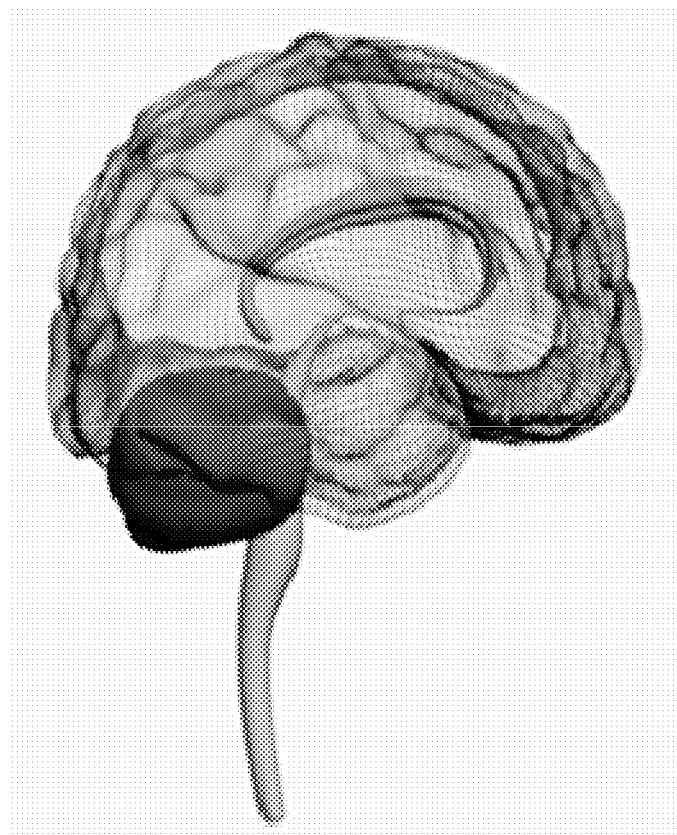

FIGS. 3, 4A, and 4B illustrate examples of a body map.

Referring to FIG. 3, a body map 310 may be a 2D image representing a horizontal cross-section of a brain. On the body map 310, anatomical structures may be indicated, and the anatomical structures may be associated with a medical diagnosis code 320, in which diagnosis names and diagnosis name codes are registered. The medical diagnosis code 320 may represent diagnosis names and diagnosis name codes identifiable by the body map 310. In the medical diagnosis code 320, the diagnosis name may be, for example, 'Disease A, Disease B, Disease C, . . . Disease F', each matching a corresponding diagnosis name code, for example, 451037005 so as to be included.

An image A 330 and an image B 340 may be medical images.

An example of acquiring medical information from an image using a body map is described as follows.

The medical information providing apparatus 100 may extract medical information associated with an area in which the body map 310 is registered with the image A 330. The image A 330 may have an anatomical area classified based on coordinates similarly to the body map 310, and may be a medical image including a diagnosis name and a diagnosis name code.

The image B 340 may be a new medical image which cannot provide anatomical, coordinates, and medical information. Therefore, the image B 340 may be a medical image that medical information cannot be extracted with respect to a predetermined area by using only the image B 340. However, by registering the image B 340 to one of the body map 310 and the image A 330, the medical information providing apparatus 100 may extract medical information. After registering the image B 340 to one of the body map 310 and the image A 330, the medical information providing apparatus 100 may extract medical information included in the body map 310 or the image A 330 with respect to a lesion image on the image B 340. After that, the medical information providing apparatus 100 may display each pixel of the lesion image on the body map 310 or the image A 330. A difference between the body map 310 and the image A 330 may be difference in recognizability by a user. For example, the body map 310 may be a 2D illustration and the image A 330 may be a medical image. The user may selectively use an image which is easier to be recognized. As such, the image A 330 and the image B 340 may each be a medical image or an image including medical information, or a medical image to be matched to the body map 310.

The body map 310 may include at least one image or image from medical device. For example, the body map 310 may include a plurality of medical images and images arranged vertically or arranged at coordinates on an X, Y, or Z axis.

As illustrated in FIGS. 4A and 4B, a body map may be represented as a 3D image.

For example, the medical information providing apparatus 100 may include a body map in which areas are divided by a 3D mesh or voxel. Also, the body map may include a medical image to which a texture is applied to be easily recognized by a user.

FIG. 4A illustrates an example of a body map representing anatomical areas using a 3D image.

FIG. 4B illustrates an example of a cross section of body map horizontally or vertically acquired from the 3D image of FIG. 4A.

Figure 5:
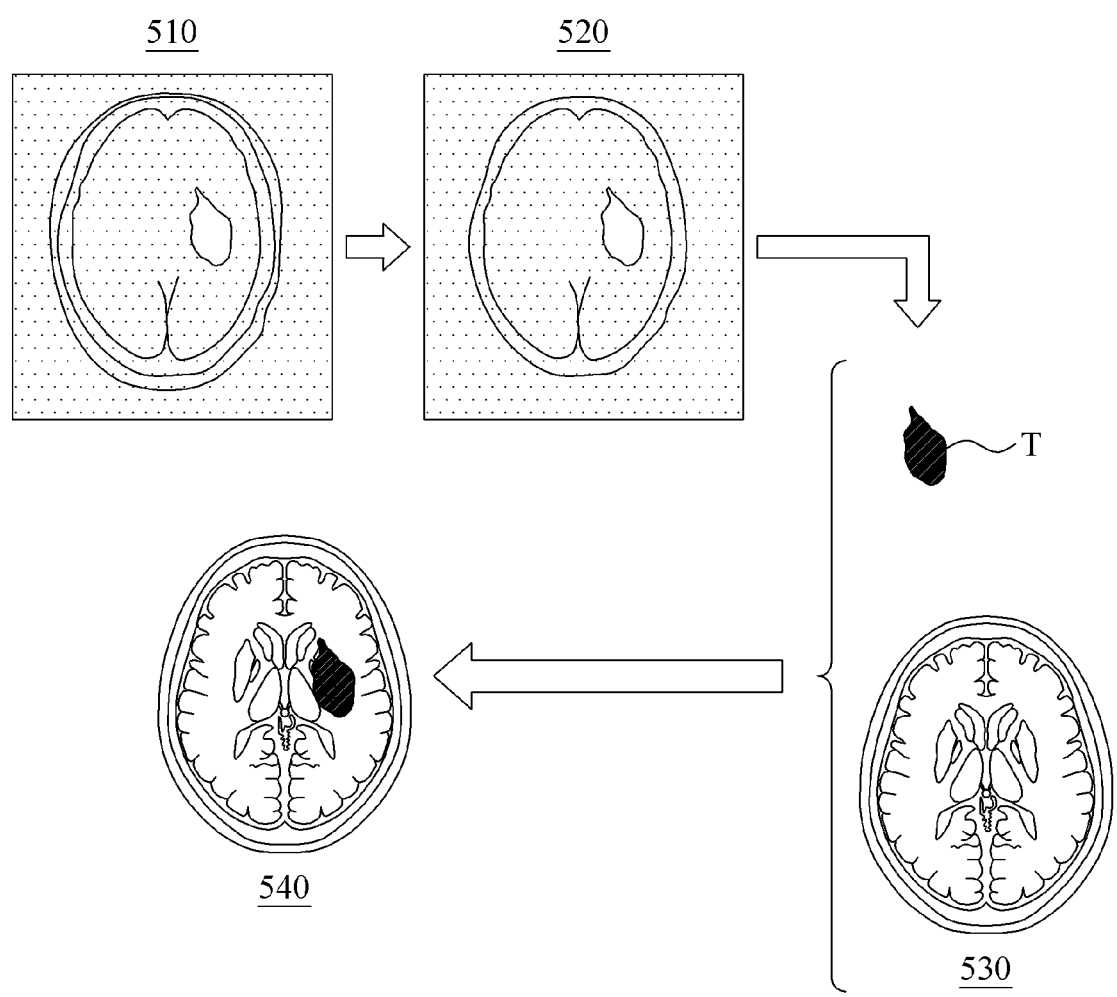
FIG. 5 is a diagram illustrating a process of extracting a lesion image and registering the lesion image with a body map according to an example embodiment.

FIG. 5 is a diagram illustrating a process of extracting a lesion image and registering the lesion image to a body map according to an example embodiment.

Hereinafter, a medical image including a bleeding lesion on the left basal ganglia of a brain will be described as example.

The extractor 120 may extract a white portion from medical images 510 and 520 as a lesion image T. The registration module 130 may register the extracted lesion image T to the corresponding anatomical region of body map 530. The registration module 130 may overlay the lesion image T on the basal ganglia of the body map 530 as indicated as a black area. Also, the registration module 130 may represent the lesion image T based on coordinates on a body map.

When it is determined that the lesion image T is distorted or partially unnecessary based on a predetermined reference, the registration module 130 may change the lesion image T or separate a portion when it is determined to be distorted or unnecessary from the lesion image T. The registration module 130 may separate the unnecessary portion from the lesion image T or change the distorted portion such that the lesion image T is registered to the body map 530.

The registration module 130 may determine the lesion image to be distorted or unnecessary and change the lesion image or separate a portion of the lesion image in the following cases. For example, in a case in which the extracted lesion image is not sufficient to express a lesion, in a case in which the extracted lesion image includes a normal tissue, in a case in which a post-treatment lesion image is extracted in duplicate with a pre-treatment lesion image, and in a case in which an excessively small or large lesion image is extracted, the registration module 130 may change the lesion image or separate a portion of the lesion image. When separating the portion of the lesion image, the registration module 130 may divide the lesion image into numerous areas and perform individual registration on each of the areas. The reference is not limited to the foregoing example and may be determined or changed by an operator. An example of a process of changing a lesion image will be described with reference to FIGS. 6 through 8B.

Figure 6:
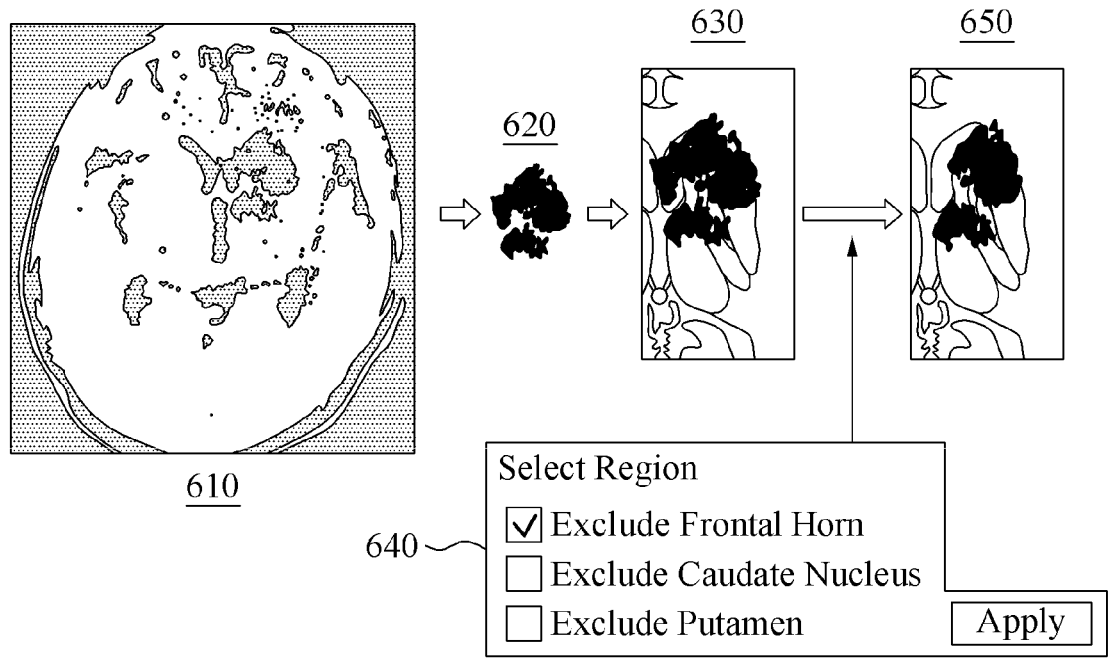
FIGS. 6 and 7 are diagrams illustrating a process of changing a lesion image according to an example embodiment.
Figure 7:
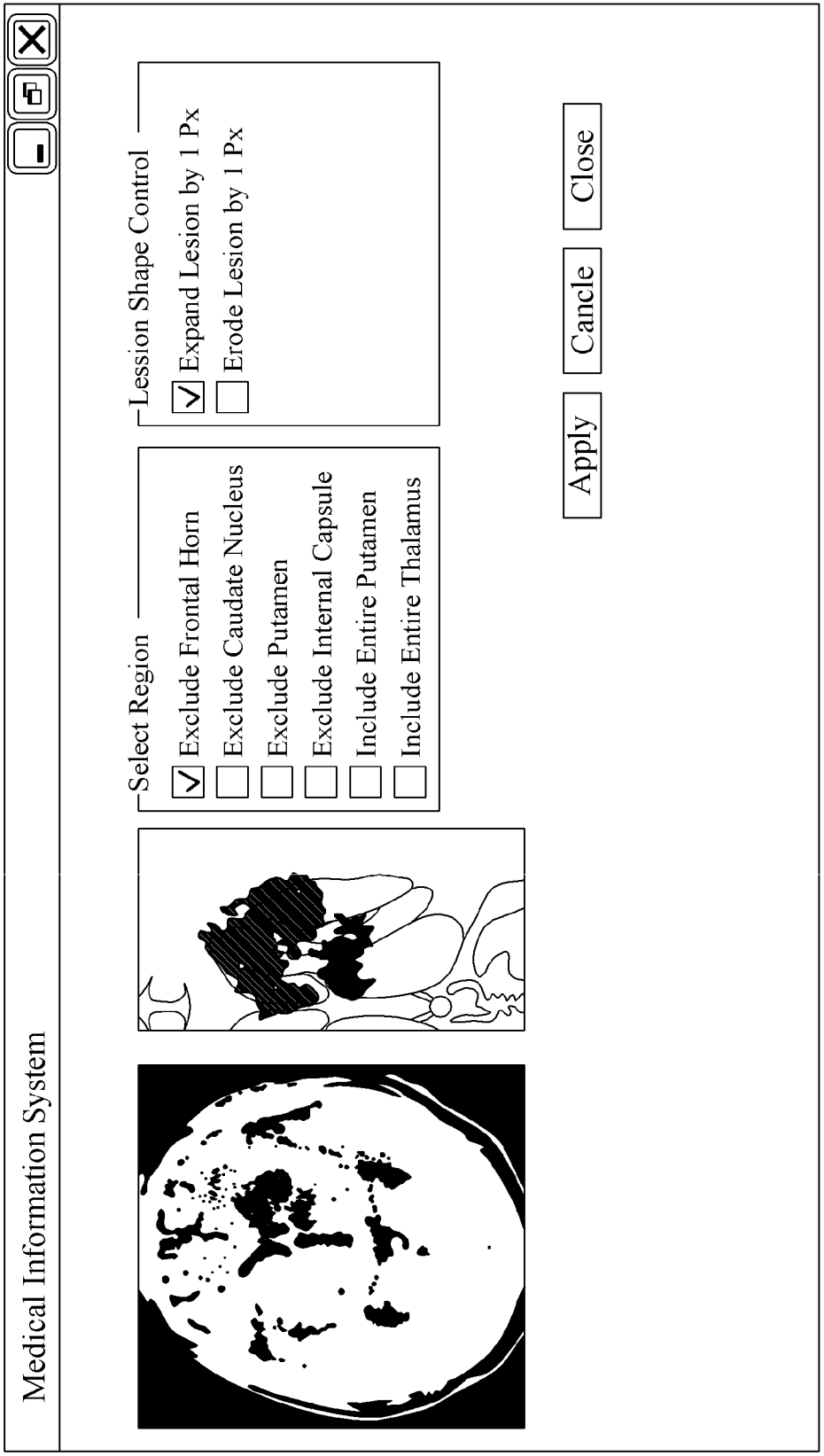

FIGS. 6 and 7 are diagrams illustrating a process of changing a lesion image according to an example embodiment.

The extractor 120 may extract a lesion image 620 from a medical image 610. The extracted lesion image 620 may be registered to a body map by the registration module 130 as indicated by a reference numeral 630. In this example, the registration module 130 may register the lesion image to an anatomically corresponding area on the body map.

When the lesion image includes an area of non-pathologic tissues, a lesion may be incorrectly expressed and thus, incorrect medical information may be extracted. In this example, the registration module 130 may change the lesion image and perform registration on the changed lesion image as indicated by a reference numeral 640. The registration module 130 may change the lesion image to correspond to the anatomical area on the body map and perform the registration on the lesion image as indicated by a reference numeral 650.

Also, the registration module 130 may display an interface to select and adjust a lesion area. The registration module 130 may change the size of a lesion image based on an adjustment value of the lesion image by the input through the interface 700. For example, as illustrated in FIG. 7, the registration module 130 may allow the interface 700 used for selecting an anatomical name or term of the corresponding area to be displayed.

The extractor 120 and the registration module 130 may repetitively perform an extracting and registration process until the lesion image is precisely extracted and the lesion image is appropriately registered to the body map. The registration-process may include a process of laying the lesion image on the body map and a process of adjusting the body map to the lesion image. The extractor 120 and the registration module 130 may perform operations in various orders. For example, the extractor 120 and the registration module 130 may extract the lesion image after registering the medical image to the body map, or extract the lesion image and then register the lesion image to the body map.

Figure 8A:
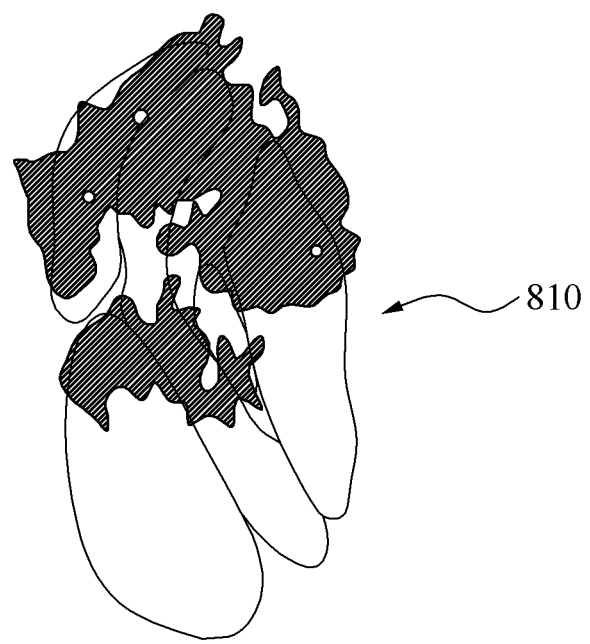
FIGS. 8A and 8B are diagrams illustrating examples of dividing a lesion image to perform registration to body map.
Figure 8B:
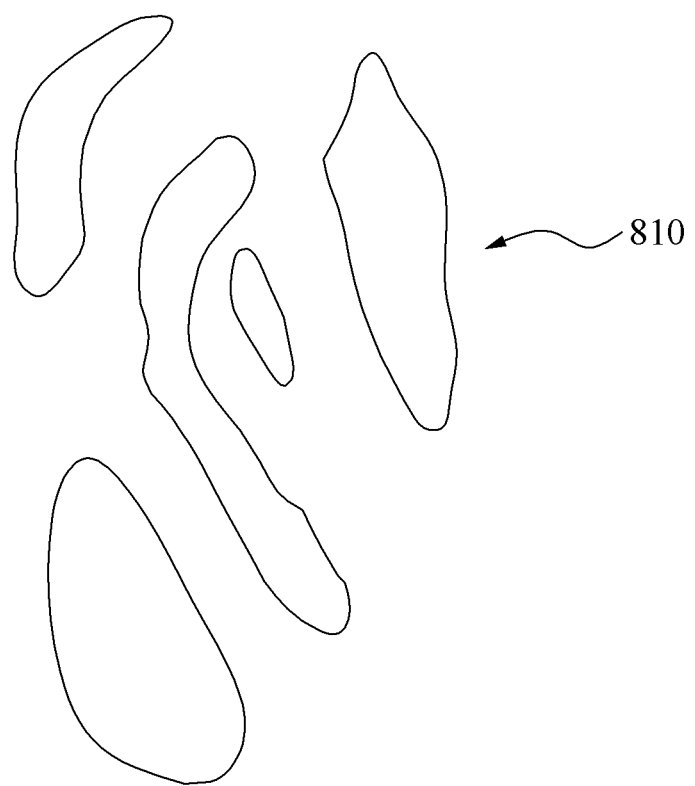

FIGS. 8A and 8B are diagrams illustrating examples of dividing a lesion image to perform registration of the lesion image.

FIGS. 8A and 8B illustrate a process of dividing a lesion image into pieces using the registration module 130.

FIGS. 8A and 8B illustrate 'brain' as an example, but are not limited thereto.

FIG. 8A illustrates a brain region 810 anatomically divided to extract a lesion image. In this example, when registration is performed on an anatomically wide area, some portion cannot be registered. Thus, as illustrated in FIG. 8B, the registration module 130 may separate the region 810 to perform precise registration. Through such separating process, an error rate may be reduced when displaying medical information associated with the lesion image.

Referring back to FIG. 1, the processor 140 may display medical information of a lesion image. That is, the processor 140 may display medical information included in an area of a body map corresponding to a lesion image.

The processor 140 may display the medical information associated with the lesion image. For example, the processor 140 may display medical information associated with a disease that may occur in an extracted lesion image.

The processor 140 may display the medical information including at least one piece of medical information among an anatomical name, a diagnosis, a terminology code for the diagnosis, and a medication for treatment of the lesion image.

Figure 9:
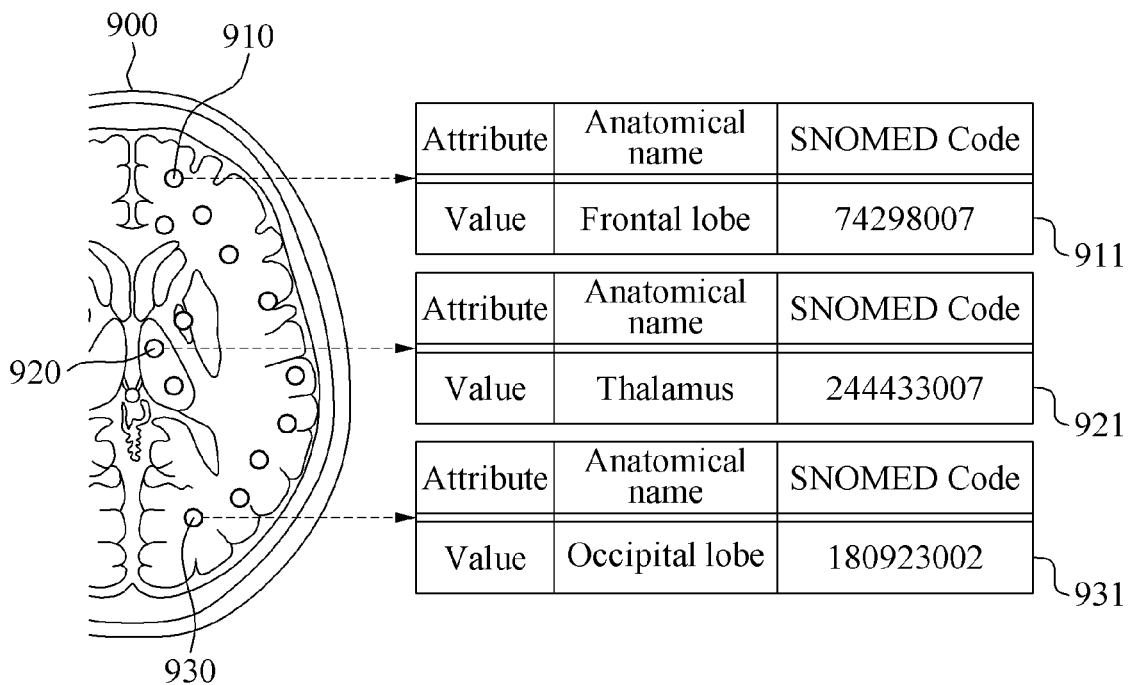

FIGS. 9 and 10 are diagrams illustrating examples of a body map with attribute nodes.

A plurality of attribute nodes 910, 920, 930 may be applied on a body map 900.

The processor 140 may display medical information 911, 921, and 931 read from a database using at least one of the verified attribute nodes 910, 920, and 930. In other words, the processor 140 may display the medical information 911, 921, and 931 by applying the body map 900 equipped with multiple attribute nodes 910, 920, and 930.

As illustrated in FIG. 9, the attribute nodes 910, 920, and 930 may be mapped to a 2D image, and each of the attribute nodes 910, 920, and 930 may include medical information associated with the corresponding anatomical areas.

Each of the attribute nodes 910, 920, and 930 may have attributes to be used for extracting medical information such as a body organ, a diagnosis name, and the like.

For example, the attribute nodes 910, 920, and 930 may be mapped to the body map 900 corresponding to a 2D image of a brain, and each of the attribute nodes 910, 920, and 930 may include 'anatomical name' and 'SNOMED Code' as medical information associated with an anatomical area. Among the attribute nodes 910, 920, and 930, an area having an anatomical name of 'Frontal lobe' may have 'SNOMED Code' of '74298007' as shown in a table 911, an area having an anatomical name of 'Thalamus' may have 'SNOMED Code' of '244433007' as shown in a table 921, an area having an anatomical name of 'Occipital lobe' may have 'SNOMED Code' of '180923002' as shown in a table 931. Also, the attribute nodes 910, 920, and 930 may include medical information, for example, a body organ, a diagnosis name, and the like.

Although FIG. 9 illustrates the attribute nodes 910, 920, and 930 using circles, the attribute nodes 910, 920, and 930 may also be provided based on at least one combination of a point, a line, a plane, a polygon, a mathematical formula, a 3D shape, and a volume.

FIG. 10 illustrates an example of a body map with attributes in a 3D image.

As illustrated in FIG. 10, a 3D image body map 1000 may be formed by three-dimensionally mapping a plurality of attribute nodes 1020 to a 2D image. body map 1010. In this example, the attribute nodes 1020 may be regularly or irregularly distributed attribute nodes.

For example, in the attribute nodes 1020, attribute grids 1030 mapped to an extracted 3D image lesion image 1040 at predetermined intervals defined by body map may be distributed. The attribute nodes 1020 within the 3D image lesion image 1040 may be used to extract medical information.

The 3D image body map 1000 may be provided as a body map to which attribute nodes are applied and thus, may be used to extract medical information based on values of attribute grids within a lesion area.

Figure 11:
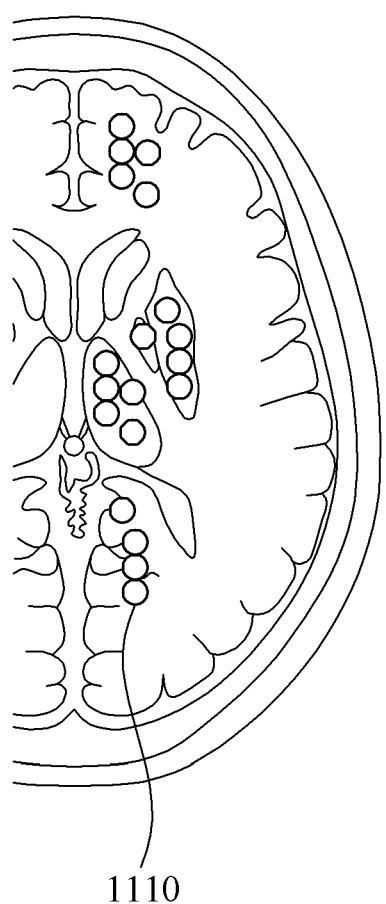
FIG. 11 is a diagram illustrating an example of attribute nodes with irregular arrangement in human body map according to an example embodiment.

FIG. 11 is a diagram illustrating an example of attribute nodes with irregular arrangement in body map according to an example embodiment.

Attribute nodes 1110 may be irregularly mapped to a body map 1100 based on an importance. For example, as an importance of an area increases, the attribute nodes 1110 may be mapped with a higher density to be on the body map 1100. Also, as an importance of an area decreases, the attribute nodes 1110 may be mapped with a lower density. In this example, at least one of the attribute nodes 1110 may be mapped on the body map 1100.

In this disclosure, an attribute node may be provided based on at least one combination of a point, a line, a plane, a polygon, a mathematical formula, a 3D shape, and a volume and may not be limited in terms of shape. Although FIG. 9 illustrates the attribute node as a sphere, a shape of the attribute node may be, but not limited to, a circle, a quadrangle, a hexagon, and a star-shape. Also, the attribute node may have an irregular shape or each attribute node has a different shape.

Hereinafter, an example of verifying attribute nodes included in a registered area and displaying medical information using the processor 140 will be described with reference to FIG. 12.

Figure 12:
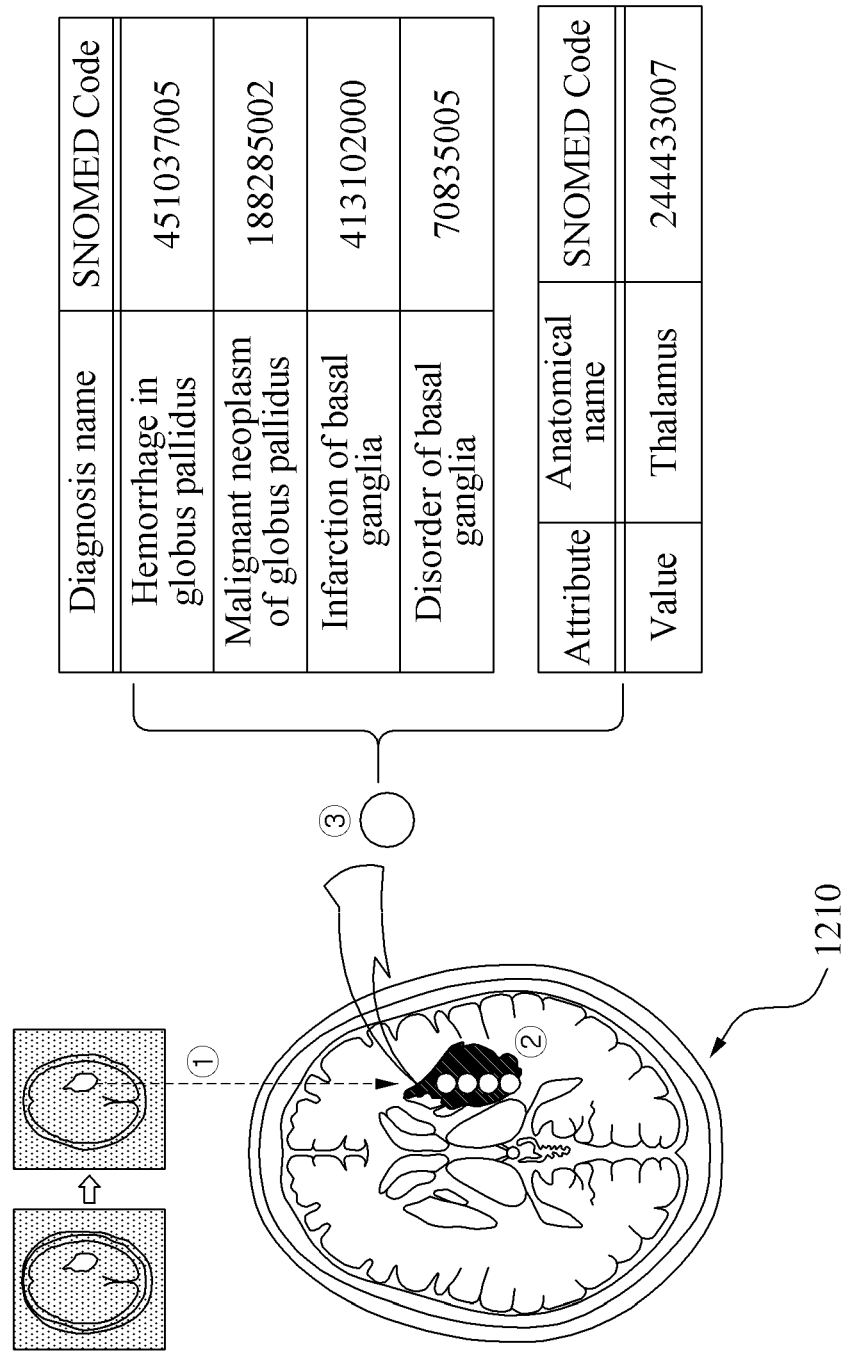
FIG. 12 is a diagram illustrating a process of displaying medical information using an attribute node in a human body model registered with a lesion image according to an example embodiment.

FIG. 12 is a diagram illustrating a process of displaying medical information using an attribute node on a body map which is registered with a lesion image according to an example embodiment.

In operation 1, the extractor 120 may extract a lesion image from a medical image. For example, the extractor 120 may extract a white portion from a medical image capturing a cross section of a brain as a lesion image.

In operation 2, the registration module 130 may register the extracted lesion image and a body map 1210, for example, a brain image model. For example, the registration module 130 may register the extracted lesion image on an anatomical area of the body map 1210.

In operation 3, the processor 140 may verify an attribute node within a registered area and read medical information corresponding to the attribute node from a database. FIG. 12 illustrates an example of mapping 4 attribute nodes to a registered area. The processor 140 may display the medical information included in a predetermined attribute node or a plurality of attribute nodes as shown in a table of FIG. 12. In this example, as the medical information, 'diagnosis name' and 'SNOMED code', or 'anatomical name' and 'SNOMED code' may be displayed. For example, the processor 140 may display at least one piece of medical information including 'SNOMED code'.

The medical information providing apparatus 100 may display medical information associated with a 2D lesion image or a 3D lesion image mapped to an attribute node, thereby reducing a time for searching for the medical information including a diagnosis name and a terminology system code of the lesion image and recording the medical information.

Figure 13:
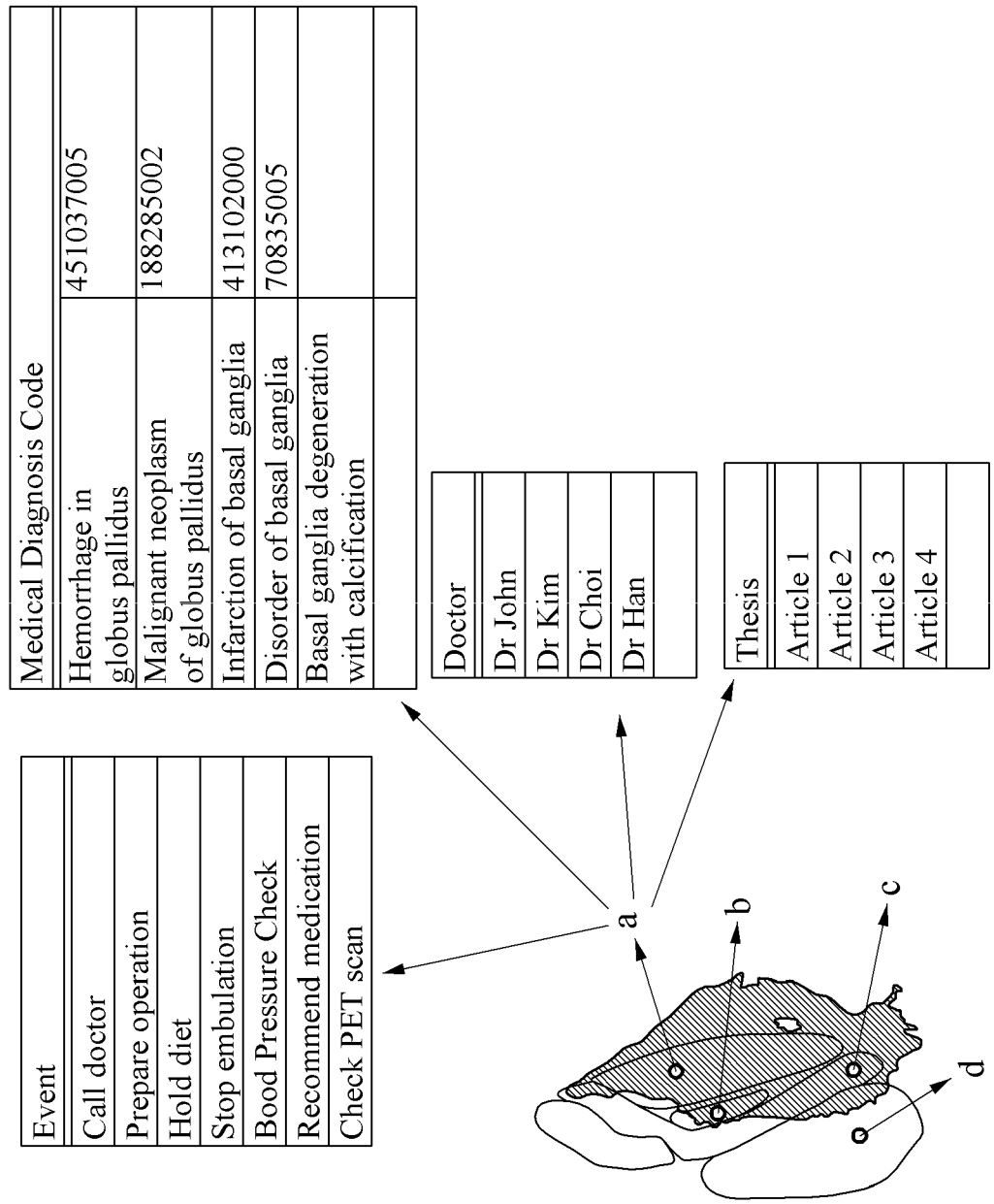
FIG. 13 is a diagram illustrating an example of displaying medical information using a lesion area and an attribute node on a body map registered with a lesion image according to an example embodiment.

FIG. 13 is a diagram illustrating an example of displaying medical information using an attribute node on a body map registered with a lesion image according to an example embodiment.

In the body map with a plurality of attribute nodes, an affected area surrounding each of the plurality of attribute nodes may be registered. The processor 140 may verify an affected area of which at least a portion overlaps the registered area, and at least one attribute node corresponding to the affected area. Also, the processor 140 may display medical information read from a database using the verified attribute node.

A shaded portion of FIG. 13 represents a registered lesion image. A mapped portion overlapping the registered area may be an affected areas surrounding an attribute node a, an attribute node b, and an attribute node c. In FIG. 12, the registered area may overlap three attribute nodes. Here, the affected area may be set by anatomical definition. An affected area including the attribute node b may represent, for example the globus pallidus.

The processor 140 may verify an attribute node which is mapped to or overlapping the registered area. In this example, the attribute node a, the attribute node b, the attribute node c may be mapped to the registered area. The node d may not be mapped to the registered area. Thus, the processor 140 may not display medical information associated with the attribute node d. The processor 140 may verify the attribute node a, the attribute node b, and the attribute node c and display medical information corresponding to each of the attribute nodes a, b, and c.

The processor 140 may determine a display position and a display size of the medical information in consideration of the size of the registered area. The processor 140 may appropriately adjust the display position and the display size on a screen on which the medical information is to be displayed.

Also, in response to the displayed medical information being selected, the processor 140 may search the database for detailed medical information associated with the selected medical information and display the detailed medical information.

As illustrated in FIG. 13, the processor 140 may display the medical information associated with the attribute node a. In this example, the processor 140 may display a diagnosis name and a diagnosis name code as shown in a table of 'medical diagnosis code'. The processor 140 may display medical information and detailed medical information associated with tables of 'event', 'doctor' and 'thesis'.

In one example, when an item 'call doctor' is selected from the table of 'event', the processor 140 may display a contact of a doctor in charge or a program for calling the doctor. The processor 140 may display an item, for example, 'sending text to doctor's cell phone', 'calling doctor's cell phone', 'sending message to doctor's mail', and 'sending message to doctor's SNS', and deliver an emergency message with at least one of the aforementioned items.

In another example, when 'prepare operation' is selected, the processor 140 may display detailed medical information for preparing an operation. In still another example, when a thesis of medical information is selected, the processor 140 may display link information of a related thesis as the detailed medical information. In yet another example, the processor 140 may extract a plurality of diagnosis names, display the extracted diagnosis names, and display detailed medical information associated with a more accurate diagnosis name in response to the more accurate diagnosis name being selected.

In further another example, the processor 140 may display information on drugs to be prescribed as medical information based on medication information of a patient. The processor 140 may transmit information about the displayed drugs to a pharmacy in a hospital or allows information about the displayed drugs to be printed as a prescription. When a patient is classified as an emergency patient, the processor 140 may display an emergency mark as the medical information based on a result of calculation performed using a feature, for example, a brightness, a size, and a diameter, of a lesion. Also, the processor 140 may make an alarm for the emergency patient to notify the emergency in the hospital using, for example, broadcasting, a light emitting lamp, and a monitor.

Figure 14A:
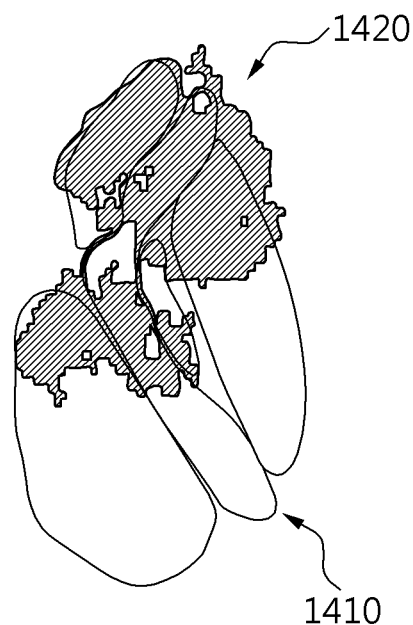
FIGS. 14A through 14C are diagrams illustrating examples of applying different weights of reliability on medical information for each attribute node according to an example embodiment.
Figure 14B:
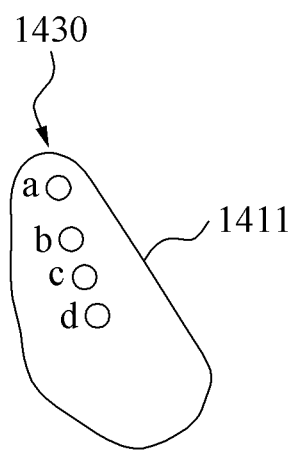
Figure 14C:
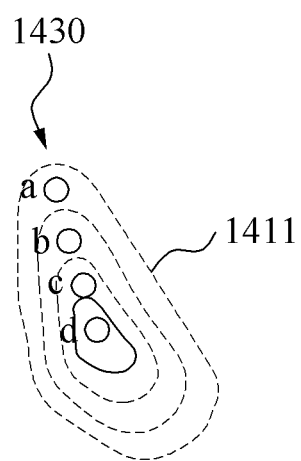

FIGS. 14A through 14C are diagrams illustrating examples of applying different weights of reliability on medical information for each attribute node according to an example embodiment.

FIGS. 14A through 14C illustrate examples of displaying medical information using attribute nodes that evaluate reliability depending on node location.

FIG. 14A is a diagram illustrating a portion of a brain when an affected area 1410 overlaps a registered area 1420. Specifically, the affected area 1410 may be an area into which a brain is anatomically divided.

FIG. 14B is a diagram illustrating a thalamus of the brain on a body map. A plurality of attribute nodes 1430 is distributed serially from the center of the anatomical structure in the body map. For example, an affected area 1411 may have 4 attribute nodes 1430. In this example, an attribute node d is the closest one to the center point, and an attribute node c, attribute node d, and attribute node a spaced apart from the attribute node d at predetermined intervals may be mapped to the affected area 1411.

When a plurality of pieces of medical information is provided, the processor 140 may display the plurality of pieces of medical information sequentially by reading plurality of pieces of medical information in the order of reliability. For example, the processor 140 may verify the attribute nodes 1430 mapping on the registered area 1420 by setting a reliability weight for each areas into which the affected area 1411 is divided based on the distance from the center point. Also, the processor 140 may display the medical information read from the database using the attribute nodes 1430 in a descending order of the reliability.

Since the attribute node a, the attribute node b, the attribute node c, and the attribute node d are included in the affected area 1411, the processor 140 may display the same medical information. However, as illustrated in FIG. 14C, the processor 140 may divide the affected area 1411 into an area based on the center point as indicated by a concentric circle. In this example, it is considered that the attribute node a, the attribute node b, the attribute node c, and the attribute node d are included in different concentric circles. As a concentric circle is closer to the center point, the processor 140 may assign a higher weight of reliability to the concentric circle. In FIG. 14C, the attribute node d may have a highest weight and the attribute node a may have a lowest weight. If the registered area 1420 includes both the attribute node d and the attribute node a, the processor 140 may determine that medical information of the attribute node d is more accurate than medical information of the attribute node a and thus, may display the medical information of the attribute node d.

Figure 15:
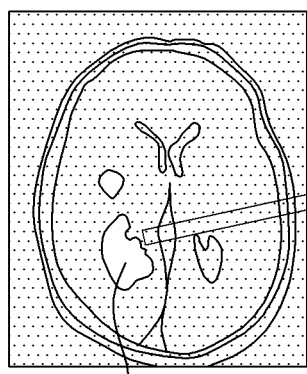
FIG. 15 is a diagram illustrating an example of displaying medical information according to an example embodiment.

FIG. 15 is a diagram illustrating an example of displaying medical information according to an example embodiment.

The processor 140 may display a code associated with features of a lesion image, for example, visual characteristics or shapes as the medical information. The processor 140 may verify characteristics of the lesion image. In FIG. 15, with respect to a lesion image 1510, the processor 140 may verify that, for example, 'lesion image is bright—246649003', 'edge is uneven—129736006', 'volume is 00—118565006', and 'bright and dark parts are mixed. Subsequently, the processor 140 may display the code associated with the form of the lesion image as the medical information. For example, the processor 140 may display a code '246649003' corresponding to a bright lesion image as the medical information.

The processor 140 may compare the lesion image and preset lesion standard images in at least one of a brightness, a size, and a similarity, and display medical information having a highest matching probability based on a result of the comparing. For example, when an attribute node includes a plurality of diagnosis names corresponding to the lesion image, the processor 140 may compare the lesion image with standard images to display medical information having a higher matching probability.

Here, the lesion standard image may be a lesion image having a feature such as a shape and a color that are used in the medical field with respect to the corresponding lesion. For example, the lesion standard image may be an image included in an illustration or a medicine textbook that explains a lesion. Also, lesion standard images may be included in a body map.

Also, the processor 140 may perform a comparison using a user selected reference or a pre-selected reference through a calculation using a brightness of a lesion, a shape of the lesion, a smoothness of a border of the lesion, and a calculation using at least one pixel brightness value as variable that consider spatial relationships between one pixel and surrounding pixels. In this example, the processor 140 may perform the comparison based on computer vision technology or image processing technology.

Figure 16A:
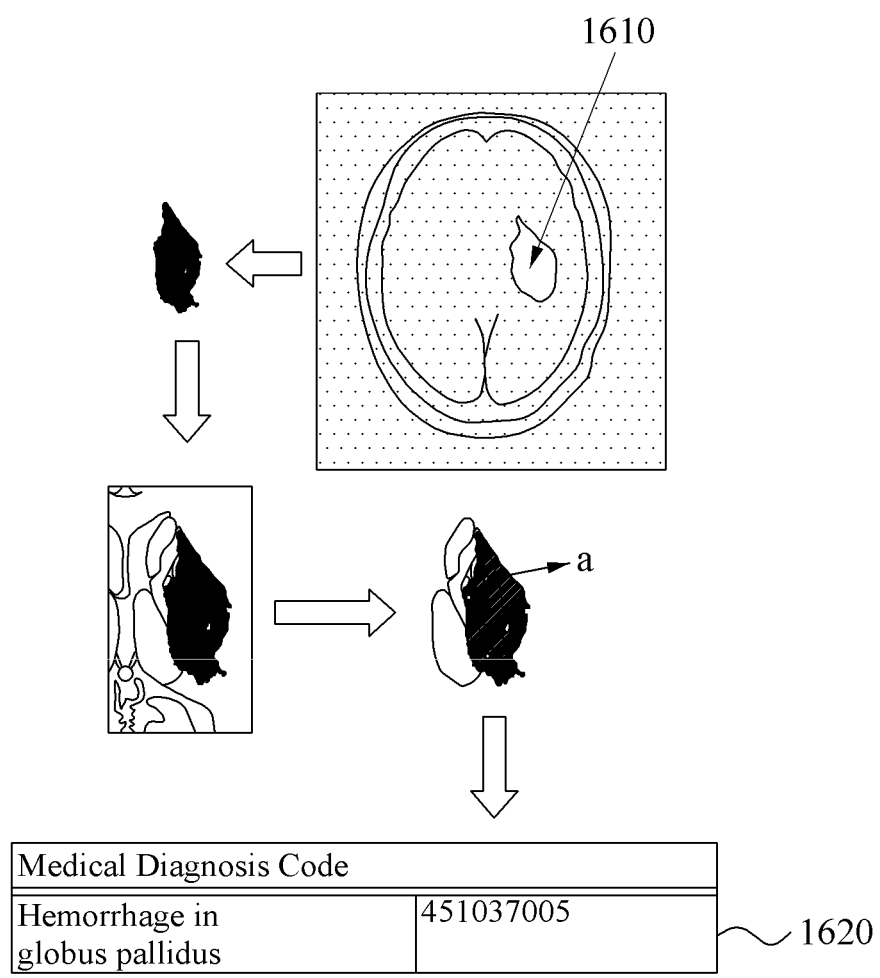
FIGS. 16A and 16B are diagrams illustrating a process of displaying medical information based on brightness in a lesion according to an example embodiment.
Figure 16B:
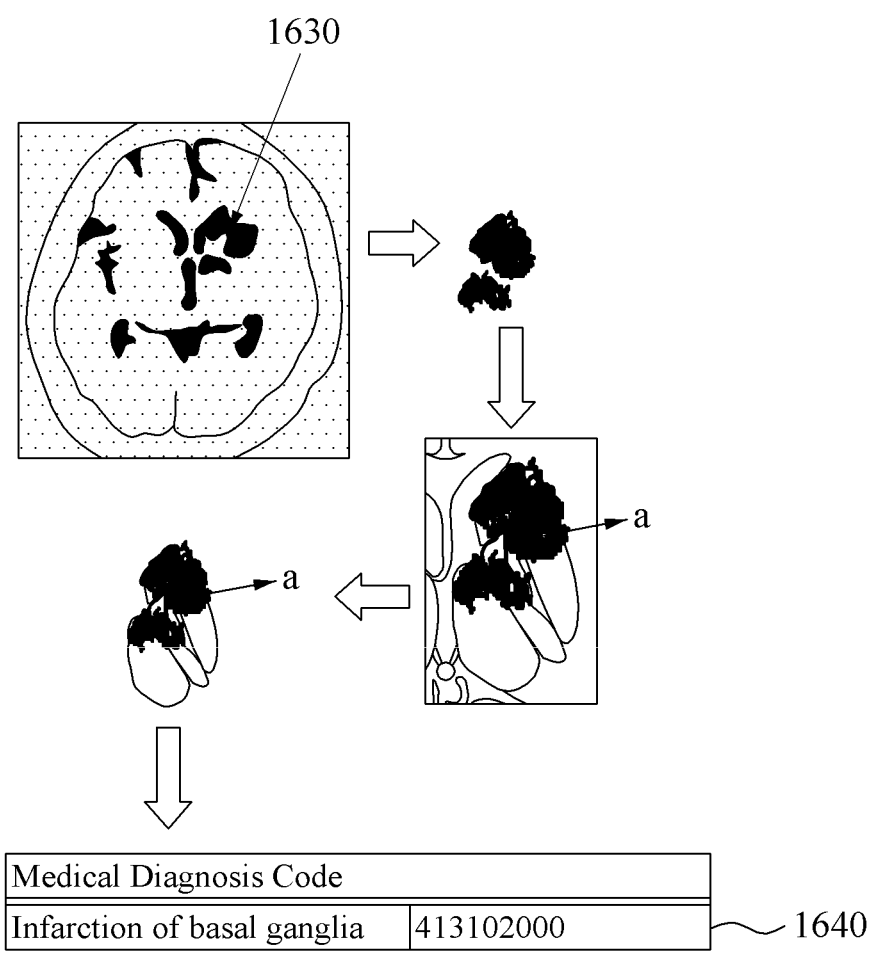

FIGS. 16A and 16B are diagrams illustrating a process of medical information based on a brightness in a lesion according to an example embodiment.

Referring to FIGS. 16A and 16B, the processor 140 may verify that the attribute node a is mapped to two different lesion images. A lesion image 1610 in a medical image of FIG. 16A may be bright and a lesion image 1630 in a medical image of FIG. 16B may be dark. The processor 140 map compare each of the lesion images 1610 and 1630 to standard lesion images (not shown), and may verify that the lesion image 1610 in the medical image of FIG. 16A is bright and the lesion image 1630 in the medical image of FIG. 16B is dark.

When a bright image in the standard lesion image is more likely to be 'brain hemorrhage', the processor 140 may display medical information about 'brain hemorrhage' with respect to the lesion image 1610 of FIG. 16A. For example, the processor 140 may display 'hemorrhage in globus pallidus' corresponding to a diagnosis name of 'brain hemorrhage' and '451037005' corresponding to a diagnosis name code of 'brain hemorrhage' as shown in a table 1620. Also, when a dark color in the standard lesion image is more likely to be 'cerebral intfarction', the processor 140 may display medical information about 'cerebral infarction' with respect to the lesion image 1630 of FIG. 16B. For example, the processor 140 may display 'infarction of basal ganglia' corresponding to a diagnosis name of 'cerebral infarction' and '413102000' corresponding to a diagnosis name code of 'cerebral infarction' as shown in a table 1640.

Referring back to FIG. 1, the storage 150 may match the lesion image and the medical information and store a result of the matching in a database. For example, the storage 150 may match the lesion image with the medical information before the lesion image is registered and match the lesion image with the medical information after the lesion image is registered so as to store the lesion image in the database. Herein the image may be represented as coordinates on the body map after the image is registered to the body map.

The storage 150 may store medical information that is included in an attribute node. For example, when a lesion image having medical information of 'brain hemorrhage' and '451037005' is displayed by the processor 140, the storage 150 may match the lesion image to the medical information and store the lesion image in association with the medical information in the database. In this example, when the medical information of the lesion image is displayed using the attribute node a, the storage 150 may store the corresponding medical information 'brain hemorrhage' and '451037005' in the attribute node a. The stored lesion image and the medical information may be used when the medical information of the corresponding lesion image is displayed.

The stored lesion image may include at least one of coordinates based on the body map, size, and shapes used in the registration and may differ from an original image in terms of a size, a shape, or coordinates thereof. For example, the lesion image may be provided in a form of 3D coordinates because a 2D legion image was registered to a 3D body map or include coordinates different from that of the original medical image. Also, the lesion image may be registered to a plurality of body maps. The lesion image may be a lesion image that has been registered to at least one body map in accordance with at least one requirement among, for example, a profession of a user, treatment purposes, an age of a patient, a race of the patient, and a disease.

The storage 150 may store at least one of the lesion image before and after the lesion image is registered to the body map in the database by associating at least one of the lesion images with the medical information. That is, the storage 150 may store the pre-registration lesion image, the post-registration lesion image, and the extracted medical information. Through this, the storage 150 may allow the stored lesion image to represent an original size and shape without restrictions.

Also, the storage 150 may store a number related at least one of the lesion image corresponding to the registered area in the body map and the attribute node. In this example, the number may be used to identify the lesion image or an attribute node mapped to a body map and may be a combination of characters, digits, symbols, or special characters.

The medical information providing apparatus 100 may store medical information in association with a lesion image to provide a database configured to display objectified and accurate medical information based on the medical information about the lesion image. Also, the lesion image on which the registration is completed may be stored for an upgrade in a terminology code system so as to easily update the medical information without need to use an extractor or a registration module.

Figure 17A:
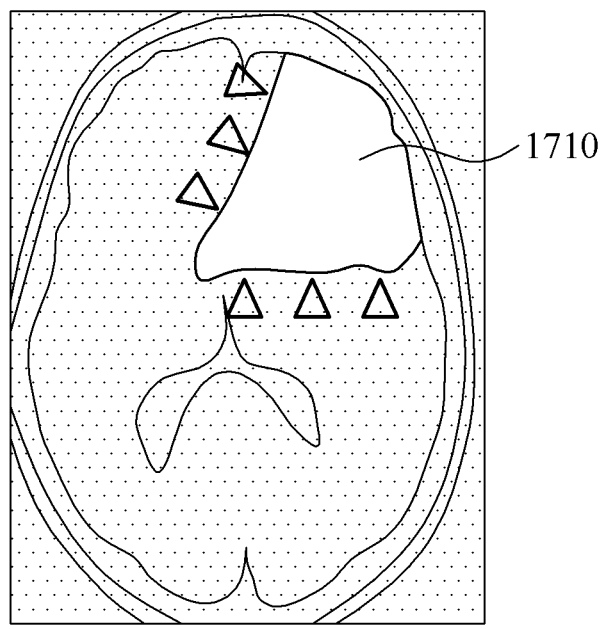
FIGS. 17A and 17B are diagrams illustrating a lesion image using a plurality of medical images according to an example embodiment.
Figure 17B:
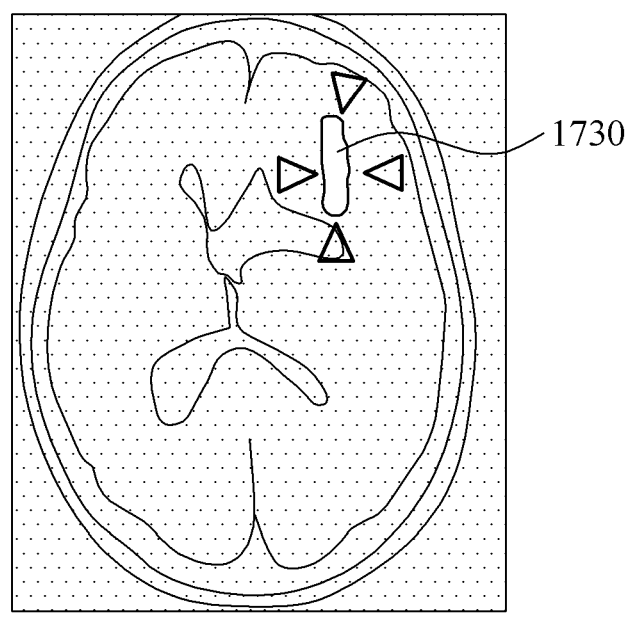

FIGS. 17A and 17B are diagrams illustrating a lesion image using a plurality of medical images according to an example embodiment.

The medical information providing apparatus 100 may extract a lesion image using a plurality of images. For example, a plurality of images may be acquired for the same patient. The acquirer 110 may acquire two medical images of the patient who has taken a CT and then another CT again using contrast agents. Additionally, when the patient takes an MRI, the acquirer 110 may acquire at least three medical images.

A size and a meaning of a lesion may be different for each of the medical images. For example, a size and a meaning of the lesion from the CT image may be different from a size and a meaning of the lesion from the MRI image. The extracted lesion images may not be consistent in view of characteristics of the image, and affected areas. From this, it is understood that sometimes with different size and the meaning of the lesion may lead to different medical information from a patient's medical images.

FIGS. 17A and 17B illustrate medical images of a patient suffering from a brain tumor. In the medical image of FIG. 17A, an overall area 1710 may be represented as a bright area. In the medical image of FIG. 17B, a tumor 1730 may be represented as a smaller bright area. As illustrated in FIG. 17A, a lesion 1710 may be shown as a large area, in an MRI T2 image. As illustrated in FIG. 17B, an actual tumor may be shown as a relatively small area, for example, the tumor 1730, in an MRIT1 enhance view.

In FIG. 17A, the lesion of the medical image may represent not only the area in which the tumor is present but also edema surrounding the lesion. Thus, it is difficult to estimate a size and a shape of the tumor using only the medical image of FIG. 17A. Both the medical images of FIGS. 17A and 17B may be required to extract a lesion image of the edema-only region of the patient. The edema-only region may correspond to an area obtained by subtracting the medical image of FIG. 17B from the medical image of FIG. 17A.

The extractor 120 may extract the lesion image to acquire a predetermined feature area by applying a computational technique to at least one medical image. For example, the extractor 120 may extract the lesion image through a process '(A−B+C)' of subtracting a extracted lesion image of an image B from a extracted lesion image of an image A and adding a extracted lesion image of an image C thereto.

Although numerous diagnosis names and medical information may provided based on characteristics of a lesion, the medical information providing apparatus 100 may clarify the lesion image and retrieve all possible lesion images. The medical information providing apparatus 100 may be used to extract the lesion image with increased sensitivity or specificity and a user may set a degree of those values thereof.

The extractor 120 may extract a position of the tumor lesion from the medical image of FIG. 17B and extract a range of the entire lesion area from the medical image of FIG. 17A. Also, in the same examination performed by capturing images at an interval of a predetermined time, the extractor 120 may extract an image by 'subtracting' a portion in which a lesion grows from a lesion in a previous image. The extractor 120 may also extract a lesion image corresponding to a difference based on an elapsed time by obtaining a reduced size through an operation of 'subtraction' after radiation treatment. Also, the extractor 120 may adopt an overlapping portion in at least two images as the lesion image, or extract the lesion image by combining various methods through an operation of 'A-B'.

The medical information providing apparatus 100 may register or extract lesion images while comparing a previous medical image and a current medical image of the same patient. In this example, the previous medical image may be created based on pre-registration coordinates and the current medical image may be created based on post-registration coordinates. The storage 150 may store or import the previous medical image of the same patient. Also, the medical information providing apparatus 100 may store records such as a brightness, a position, a variable or a magnification, and the like required for a registration process in the storage 150 and use this stored record to register a new image.

Figure 18:
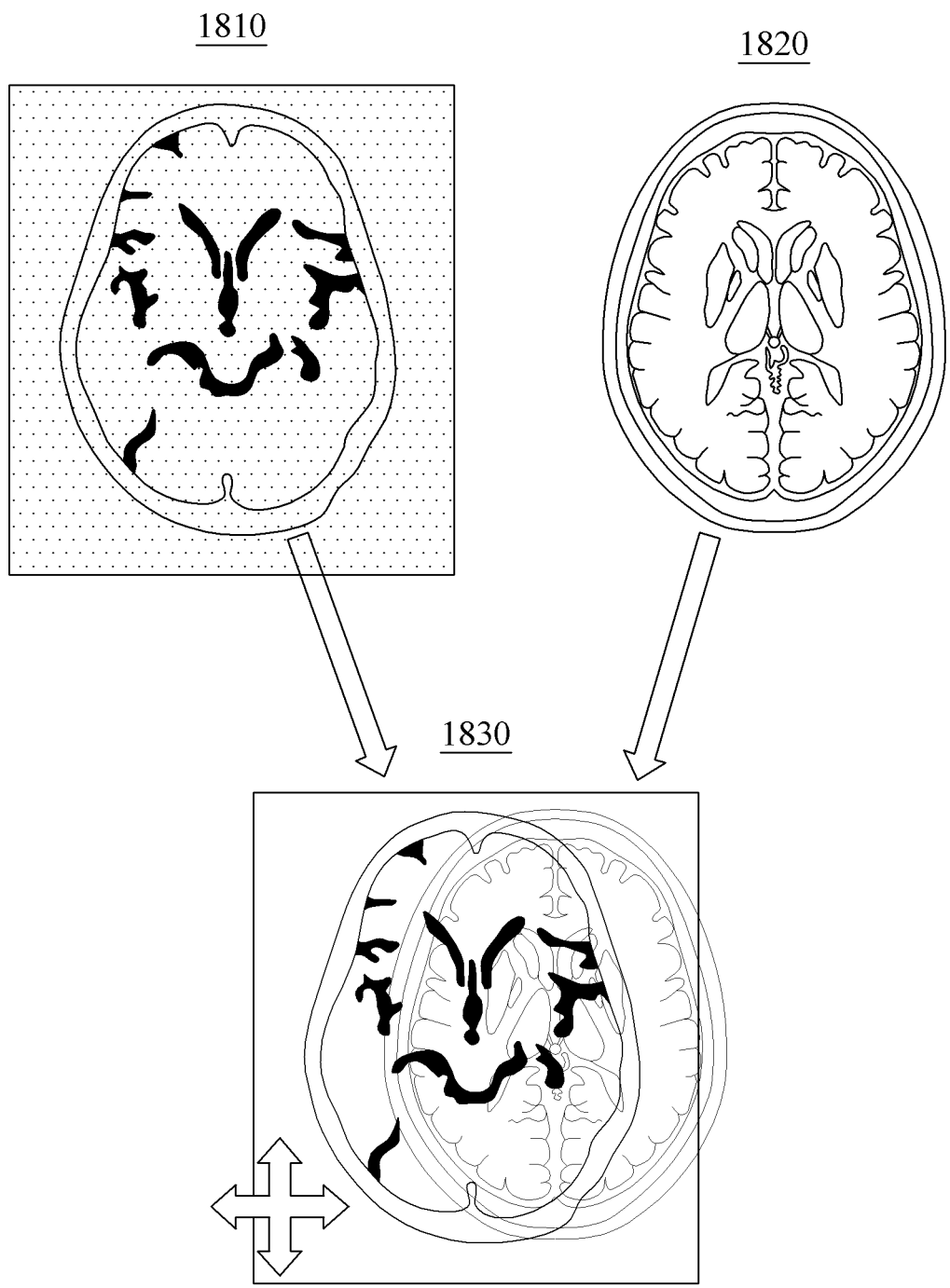
FIG. 18 is a diagram illustrating an example of a registration process of medical images by an aid of a user according to an example embodiment.

FIG. 18 is a diagram illustrating an example of a process of registering medical images by an aid of a user according to an example embodiment.

In a case in which a body map 1820 is inaccurately registered to a lesion image or a medical image 1810, the medical information providing apparatus 100 may register the medical image 1810 to a body map 1820 if a reference for registration is determined. The reference may be selected by a user or a physician. For example, when a plurality of reference medical images is provided, the user may select an image to be used as the reference, and the medical information providing apparatus 100 may perform the registration based on the selected image as indicated by a reference numeral 1830. When an overall lesion is not registered at one time, the user may select such that the registration is performed by dividing the lesion image into pieces.

Referring to FIG. 18, the medical information providing apparatus 100 may include an interface to adjust a size or a position of a medical image (a) by user or to change a size or a position of a body map (b) to perform the registration as indicated by a reference numeral 1830. Also, the medical information providing apparatus 100 may provide an interface configured to display a position on a body map or allow user to input coordinates of an affected area to assist the registration after the lesion image is extracted.

Figure 19:
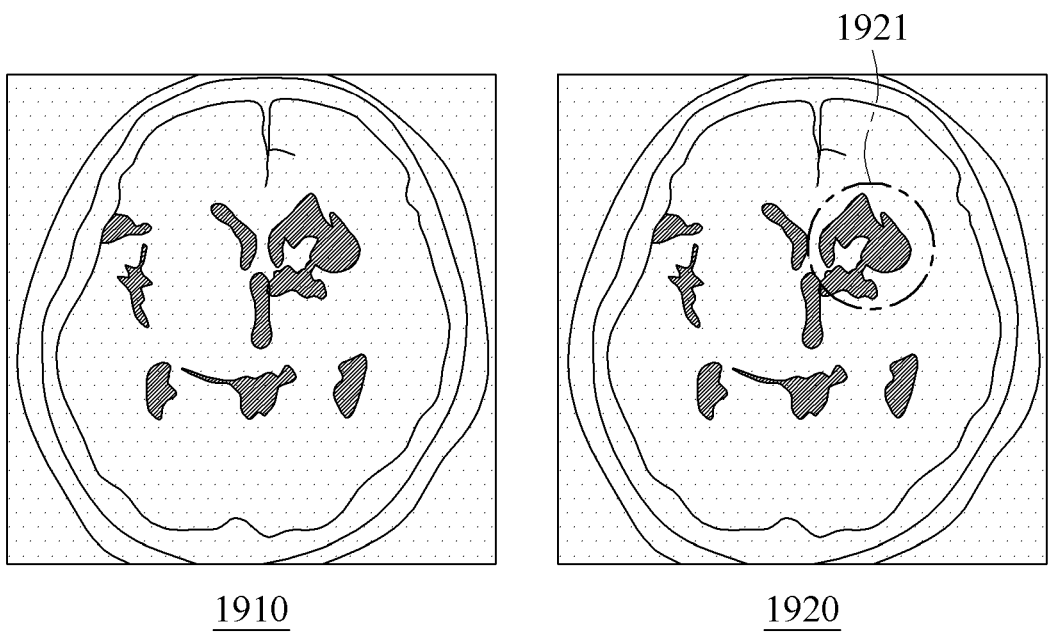

FIGS. 19 and 20 are diagrams illustrating examples of extracting a lesion image from a medical image according to an example embodiment.

FIG. 19 illustrates an example of a user setting a region of interest (ROI). The medical information providing apparatus 100 may provide an interface to set an ROI in a medical image 1910. In this example, a lesion image may be extracted from only an area 1921 in which the ROI is set other than remaining portions as indicated by a reference numeral 1920.

FIG. 20 illustrates an example of selecting a portion of an area 2020 including a lesion using a mouse in a new medical image 2010 and determining a portion of the selected portion to be a lesion as indicated by a reference numeral 2030. In this example, an eyedropper icon may indicate that information on the selected area is to be extracted. To receive brightness information of the selected area and extract the lesion image, the medical information providing apparatus 100 may find and extract an area that has a similar brightness and is connected to a designated portion without breaking.

Also, the medical information providing apparatus 100 may create a lesion image for a predetermined lesion having image characteristics no or little difference in degree of comparison when compared to a normal tissue or a body map. The medical information providing apparatus 100 may register the lesion image at a dimension estimated to be in a predetermined shape in a predetermined area of the body. In this example, the medical information providing apparatus 100 may create the lesion image based on at least one combination of a point, a line, a plane, a triangle, a polygon, a mathematical formula, and a typical anatomical structure.

The user may select the entire anatomical structure 'globus pallidus' through an interface provided from the medical information providing apparatus 100 as a lesion 1, and select a space information having coordinates of (3,19,20) and a radius of 3 in the body map as a lesion 2. Also, the user may define a lesion 3 through a combination of the lesion 1 and the lesion 2. For example, the user may create the lesion 3 by adding the lesion 1 to the lesion 2. The user may create a lesion 4 by subtracting the lesion 2 from the lesion 1. In this example, the medical information providing apparatus 100 may provide an interface to allow the user to select a diagnosis name or a diagnosis name code from the medical information or directly input a diagnosis name or a diagnosis code.

FIGS. 21 and 22 are diagrams illustrating examples of outputting a formatted document according to an example embodiment.

Referring to FIG. 21, the medical information providing apparatus 100 may extract medical information using a medical image and store a formatted document based on the medical information. The formatted document may be, for example, a radiology report.

Contents of a radiology report may have a description that records a lesion and a conclusion or an impression. The radiology report may not be drafted by a person. However, when submitting a report to a hospital or a patient is transferred to another hospital, the radiology report may be requested as a part of an electronic chart.

Referring to FIG. 22, after imaging a brain CT, production of the radiology report, extraction of a diagnosis name, or extraction of a terminology code may be performed at a time other than immediately after the image is captured. The medical information providing apparatus 100 may store a lesion image and retrieve the prestored lesion image at a time at which medical information is to be extracted. Also, the medical information providing apparatus 100 may store at least one of a pre-registration lesion image and a post-registration lesion image and extract the medical information. For example, the medical information providing apparatus 100 may store medical information on the verified lesion image in various forms such as XML and JSON in a database and print the stored medical information in a form of document.

Figure 23A:
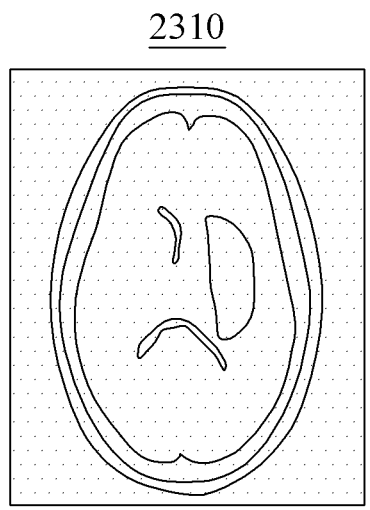
FIG. 23 is a diagram illustrating an example of predicting a shape of a lesion image according to an example embodiment.
Figure 23B:
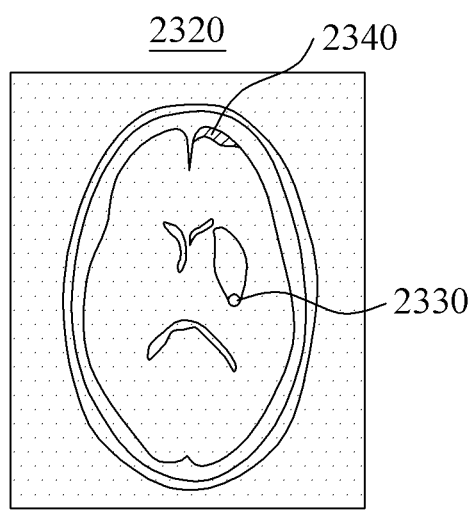

FIG. 23 is a diagram illustrating an example of predicting a shape of a lesion image according to an example embodiment.

The medical information providing apparatus 100 may extract a lesion image and predict a shape that may change based on a lesion. This may be helpful in extracting the lesion image when a lesion boundary is ambiguous. For example, when a lesion has a hemorrhage in the brain, a bleeding site may be reduced to be unremarkable after about 2 weeks. Also, in this period, a large amount of blood may be absorbed and thus, a size of the lesion may be reduced. The medical information providing apparatus 100 may extract the patient's new lesion image to reduce a volume rather than before.

Referring to FIG. 23, a medical image 2310 may be an image of a patient who has a brain hemorrhage and received surgery of inserting a catheter due to a hemorrhagic lesion. When the inserted catheter is present in a medical image 2320 and a previous surgery record is not input, a portion appear to be bright due to a drainage tube 2330 or an air containing portion 2340 may be extracted as incorrect information. The medical information providing apparatus 100 may predict values related to the drainage tube 2330 and the air containing portion 2340 appearing after the surgery using a prediction model, thereby extracting an accurate lesion image. Also, in a medical image of a brain tumor, the medical information providing apparatus 100 may predict that a volume of a lesion is to be reduced after radiation treatment or chemotherapy.

The medical information providing apparatus 100 may predict an air shading that may be seen after brain surgery in general. Through this, the medical information providing apparatus 100 may filter out an error-causing portion and accurately extract a lesion image.

Figure 24A:
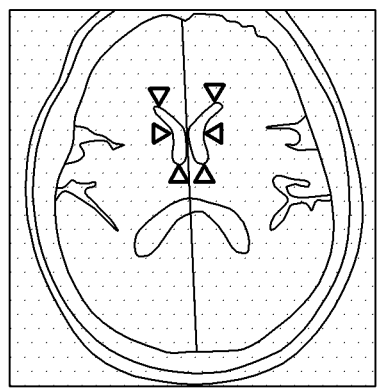
FIGS. 24A and 24B are diagrams illustrating example of selecting a body map according to an example embodiment.
Figure 24B:
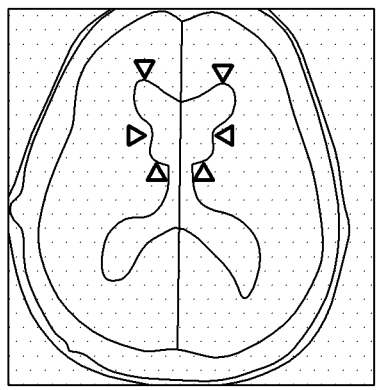

FIGS. 24A and 24B are diagrams illustrating example of selecting a body map according to an example embodiment.

A size of body may vary by individuals. For example, there may be individual characteristics such as large or small brain ventricles and large or small basal ganglia. In this example, the medical information providing apparatus 100 may select a body map based on a size of a body organ so as to be used for registration.

The medical information providing apparatus 100 may perform the registration to a body map of the small ventricle as illustrated in FIG. 24A using a body map of the large ventricle as illustrated in FIG. 24B.

In this example, in comparison to a case in which information is extracted through an overall registration of an image, an accuracy may be increased when the registration is performed by dividing a brain by parts. The medical information providing apparatus 100 may enable the registration to be performed for each brain component, and may perform registration for each component by dividing an image into pieces.

Figure 25A:
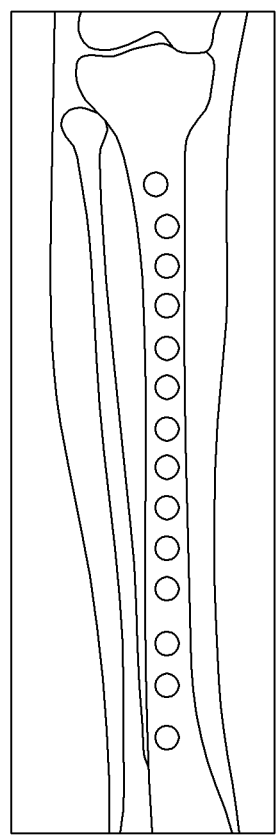
FIGS. 25A through 25C are diagrams illustrating examples of displaying medical information using an attribute node according to an example embodiment.
Figure 25B:
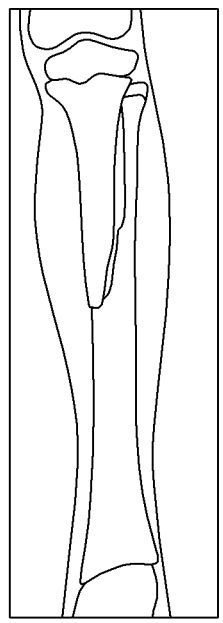
Figure 25C:
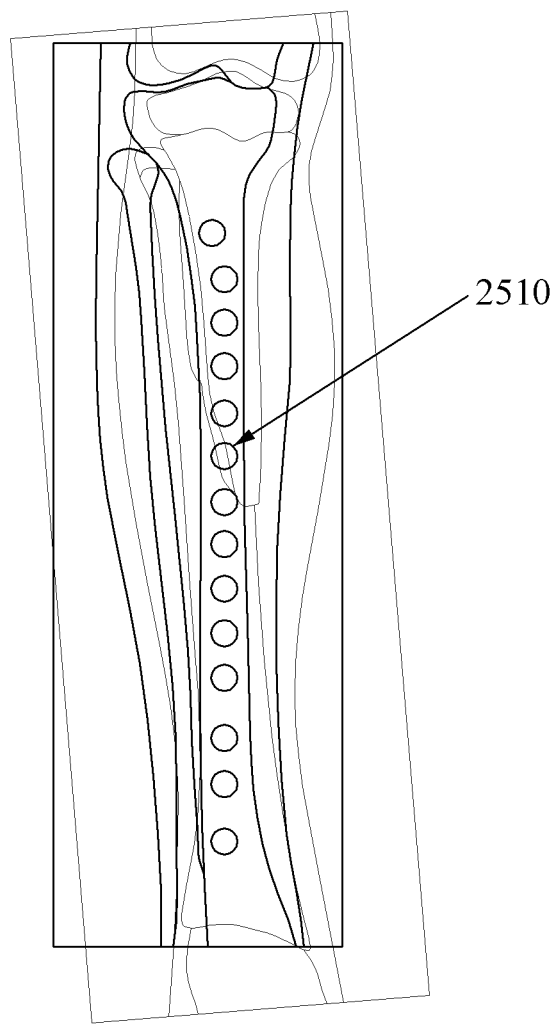

FIGS. 25A through 25C are diagrams illustrating examples of displaying medical information using an attribute node according to an example embodiment.

The medical information providing apparatus 100 may provide an interface for inputting a code related to a cause of an affected area. For example, when the tibia bone of a patient is broken due to accident, medical information may be displayed as follows.

A user or a physician may input a code '242089005' corresponding to 'traffic accident on road' to the medical information providing apparatus 100. Also, the user may verify that the patient does not have an open wound on a leg and input a code '125194009' corresponding to 'closed wound' to the medical information providing apparatus 100. From a medical image capturing a calf of the patient, the user may verify that the patient has a fracture line in shaft of the tibia. The medical information providing apparatus 100 may register the medical image of FIG. 25B and a body map of FIG. 25A in terms of length, rotate the image, and acquire an image of FIG. 25C. Also, the medical information providing apparatus 100 may identify an attribute node or a lesion node 2510 overlapping the lesion image.

The medical information providing apparatus 100 may read a value corresponding to an anatomical area among medical information included in the attribute node 2510 from the database. For example, the medical information providing apparatus 100 may read a code value '60613003' corresponding to 'an intermediate portion of the tibia'. The medical information providing apparatus 100 may display a lesion image extracted from a medical image using the code value '60613003'.

The medical information providing apparatus 100 may display the diagnosis name in consideration of all diagnosis names included in the attribute node 2510. For example, the medical information providing apparatus 100 may display at least one of diagnosis names and codes 'open fracture of shaft of tibia—6628008', 'closed fracture of shaft of tibia-26442006' and 'fracture of shaft of tibia—54441004', which are to be extracted when a shaft of tibia is broken, as the diagnosis name. In this example, the medical information providing apparatus 100 may display a diagnosis name having a greatest probability based on an input code such as 'traffic accident on road' and 'closed wound' as the medical information. For example, the medical information providing apparatus 100 may display 'closed fracture of shaft of tibia—26442006' as the diagnosis name and detail medical information corresponding thereto.

The medical information providing apparatus 100 may display to prescribe at least one of 'train to be stabilized—38588507', 'pain control—408950005', and 'long leg cast—118397005', which are extractable codes as a therapeutic treatment in a case of "open fracture of shaft of tibia'. Also, the medical information providing apparatus 100 may allow a prescription for the medication to be printed. As the prescription for 'closed fracture of shaft of tibia', the medical information providing apparatus 100 may read a stored value corresponding to a closed manual reduction from the database and display a prescription of '439217005'.

Figure 26:
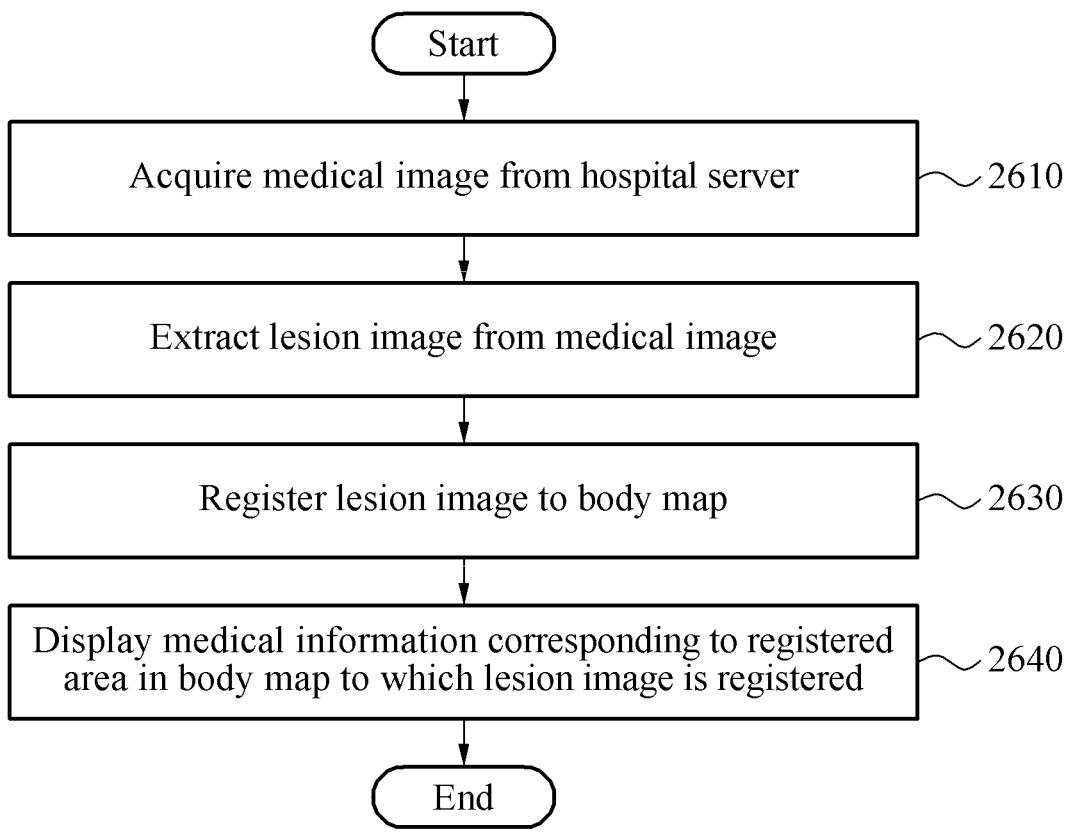
FIG. 26 is a flowchart illustrating an operation method of a medical information providing apparatus according to an example embodiment.

FIG. 26 is a flowchart illustrating an operation method of a medical information providing apparatus according to an example embodiment.

A medical information providing method may be performed by the medical information providing apparatus 100.

In operation 2610, the medical information providing method may acquire a medical image from a hospital server. Here, the medical image may be an image acquired by at least one medical imaging device or data stored in the hospital server. The image acquired by the medical imaging device may be an image captured through, for example, X-ray imaging, CT, MRI, SPECT, and PET but not limited thereto.

In operation 2620, the medical information providing method may extract a lesion image from the medical image. For example, an image suspected to be a lesion may be extracted from the medical image. In this example, the lesion image may be at least one of a 2D image and a 3D image.

In operation 2630, the medical information providing method may register the lesion image to a body map. In operation 2430, the medical information providing apparatus 100 may register the lesion image and a body map associated with a body organ corresponding to the lesion image.

Operations 2620 and 2630 may be performed in various orders. Also, Operations 2620 and 2630 may be performed repetitively. For example, the medical information providing apparatus 100 may perform operation 2630 after operation 2620 or perform operation 2630 after operation 2620. To increase accuracy, the medical information providing apparatus 100 may perform such process repetitively.

In operation 2640, the medical information providing method may display medical information corresponding to a registered area in the body map to which the lesion image is registered. For example, in operation 2640, the medical information providing apparatus 100 may display medical information included in an area corresponding to the lesion image in the body map.

Also, a plurality of attribute nodes may be mapped to the body map. In operation 2640, the medical information providing apparatus 100 may verify an attribute node to be mapped in the registered area and display medical information read from a database using the verified attribute node. Also, in operation 2640, the medical information providing apparatus 100 may display medical information associate with a registered area using a body map on which a plurality of attribute nodes are mapped.

In addition to the plurality of attribute nodes, an affected area surrounding each of the attribute nodes may be mapped to the body map. In operation 2640, the medical information providing apparatus 100 may verify an affected area of which at least a portion overlaps the registered area and an attribute node corresponding to the affected area, and display medical information read from a database using the verified attribute node.

Also, in operation 2640, the medical information providing apparatus 100 may determine a display size and a display position with respect to the medical information based on an area of the portion overlapping the registered area. For example, in operation 2640, the medical information providing apparatus 100 may appropriately adjust the display position and the display size on a screen for displaying the medical information.

In the affected area, the plurality of attribute nodes may be spaced apart based on a center point of the affected area so as to be mapped. In this example, in operation 2640, the medical information providing apparatus 100 may verify the attribute node mapped in the registered area by setting a weight of reliability for each area of the affected area based on the distance from the center point, and display the medical information read from the database using the attribute node in a descending order of weights.

In response to the displayed medical information being selected, the medical information providing apparatus 100 may search a database for detailed medical information associated with the selected medical information and display the detailed medical information. For example, when 'Prepare operation' is selected, the medical information providing apparatus 100 may display detailed medical information for preparing an operation. When a thesis of the medical information is selected, the medical information providing apparatus 100 may display link information of the thesis as the detailed medical information. The medical information providing apparatus 100 may extract a plurality of diagnosis names and display the plurality of diagnosis names. In this example, when a diagnosis is user-selected, the medical information providing apparatus 100 may display detailed medical information associated with the diagnosis. The medical information providing apparatus 100 may display information on drugs as the medical information based on medication information of a patient. Also, when a patient is classified as an emergency patient, the medical information providing apparatus 100 may display an emergency mark as the medical information based on a result of calculation performed using a feature, for example, a brightness, a size, and a diameter, of a lesion.

In the medical information providing method, medical information on a 2D or 3D lesion image mapped to an attribute node may be displayed to reduce a time for searching for medical information including a diagnosis name and a terminology system code associated with the lesion image and recording the medical information.

In the medical information providing method, medical information in a lesion image registered to a body map on which an attribute node is mapped may be displayed to accurately and easily acquire medical information including a diagnosis name and a diagnosis code.

In the medical information providing method, medical information associated with a lesion image may be stored to provide a database configured to display objectified and accurate medical information. Also, the lesion image on which the registration is completed may be stored for an upgrade in a terminology system so as to easily update the medical information without need to use an extractor and a registration module.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents.

Accordingly, other implementations are within the scope of the following claims.

The invention claimed is:

1. An apparatus for providing medical information, the apparatus comprising:
    an acquirer configured to acquire a medical image from a hospital server;
    an extractor configured to extract a lesion image from the medical image;
    a registration module configured to register the lesion image to a body map, wherein the body map is mapped with an attribute node and an affected area surrounding the attribute node; and
    a processor configured to:
        verify a plurality of attribute nodes with a patient region being overlapped and mapped to match the image of the lesion,
        set a weight for each of the plurality of attribute nodes, depending on a distance from a center point of the affected area,
        sequentially display a plurality of pieces of medical information read from a database by the plurality of attribute nodes in a descending order of the weights, and
        determine a display size and a display position with respect to the pieces of medical information based on an area of the portion overlapping the registered area.

2. The apparatus of claim 1, wherein, in response to the displayed medical information being selected, the processor is configured to search the database for detailed medical information associated with the selected medical information and display the detailed medical information.

3. The apparatus of claim 1, wherein the extractor is configured to:
    compare the medical image and a preset standard lesion image with respect to at least one of a brightness, a size, and a similarity; and
    extract, as the lesion image, a portion of the medical image having a greatest matching probability based on a result of the comparing.

4. The apparatus of claim 1, wherein the processor is configured to display the medical information associated with the legion image.

5. The apparatus of claim 1, wherein the registration module is configured to register the legion image to a body map associated with a body organ corresponding to the lesion image.

6. The apparatus of claim 1, wherein when the extracted lesion image is determined to be distorted or partially unnecessary based on a selection reference, the registration module is configured to change the lesion image or separate a portion of the lesion image determined to be distorted or unnecessary from the lesion image.

7. The apparatus of claim 1, further comprising:
    a storage configured to store at least one of the lesion image before the lesion image is registered to the body map and the lesion image after the lesion image is registered to the body map in the database.

8. The apparatus of claim 7, wherein the storage is configured to match the lesion image to the medical information before the lesion image is registered to the body map and match the lesion image to the medical information after the lesion image is registered to the body map so as to store the lesion image in the database.

9. The apparatus of claim 7, wherein, after the lesion image is registered to the body map, the lesion image is represented as coordinates on the body map.

10. The apparatus of claim 1, further comprising:
a storage configured to store a number for identifying an attribute node that is mapped to the body map or the lesion image.

11. The apparatus of claim 1, wherein the extractor is configured to extract the lesion image as at least one of a two-dimensional image and a three-dimensional image.

12. The apparatus of claim 1, wherein the processor is configured to display the medical information including at least one piece of medicine information among an anatomical name, a diagnosis name, a diagnosis name code, and a medicine for treatment corresponding to the lesion image.

* * * * *